United States Patent [19]

Kawana

[11] Patent Number: 5,620,831

[45] Date of Patent: Apr. 15, 1997

[54] CYANOGUANIDINE DERIVATIVES, AND THERMOSETTING OR PHOTOCURABLE, THERMOSETTING RESIN COMPOSITION USING THE SAME

[75] Inventor: Osamu Kawana, Sakado, Japan

[73] Assignee: Taiyo Ink Manufacturing Co., Ltd., Japan

[21] Appl. No.: 412,115

[22] Filed: Mar. 28, 1995

[30] Foreign Application Priority Data

Apr. 5, 1994 [JP] Japan .................................. 6-089191
Apr. 5, 1994 [JP] Japan .................................. 6-089192
Sep. 9, 1994 [JP] Japan .................................. 6-240833

[51] Int. Cl.$^6$ .......................... C08L 63/02; C07C 279/28; G03F 7/004
[52] U.S. Cl. ........................ 430/280.1; 522/28; 528/94; 528/93; 528/365; 528/408; 528/123; 564/104; 564/74; 564/30; 544/402; 544/96; 544/382; 549/335; 558/394; 558/430; 558/390; 558/445; 558/436; 548/331.1
[58] Field of Search ................ 548/331.1; 558/446, 558/394, 430, 390, 445, 436; 544/382, 402, 96; 549/335; 528/94, 93, 365, 408, 123; 522/28; 564/104, 74, 30; 430/280, 280.1

[56] References Cited

U.S. PATENT DOCUMENTS

| | | | |
|---|---|---|---|
| 2,455,807 | 12/1948 | Redmon et al. ........................ | 260/551 |
| 4,552,814 | 11/1985 | Cavitt et al. ............................ | 428/414 |
| 4,567,174 | 1/1986 | Edwards et al. ........................ | 514/210 |
| 4,859,761 | 8/1989 | Flury et al. ............................. | 528/123 |
| 4,912,190 | 3/1990 | Schäfer .................................. | 528/94 |
| 4,933,422 | 6/1990 | Hammer ................................ | 528/94 |
| 5,009,982 | 4/1991 | Kamayachi et al. .................... | 430/280 |
| 5,041,655 | 8/1991 | Huthmacher et al. .................. | 564/106 |
| 5,124,234 | 6/1992 | Wakata et al. .......................... | 430/280 |
| 5,387,656 | 2/1995 | Zupancic et al. ....................... | 564/104 X |

FOREIGN PATENT DOCUMENTS

| | | |
|---|---|---|
| 6471846 | 3/1964 | Japan . |
| 3289656 | 12/1991 | Japan . |
| 855017 | 11/1960 | United Kingdom .................. 544/402 |
| WO9201726 | 2/1992 | WIPO . |
| 93-10168 | 5/1993 | WIPO .................................. 528/123 |

OTHER PUBLICATIONS

Bisdiguanides Having Antibacterial Activity, Rose and G. Swain, pp. 4422–4425.
Kawana, Osamu "Synthesis of Cyanoguanidine Derivatives and thermal Curing Reaction of Epoxy Resin; Properties of the Cured Resins", *Nippon Kagaku Kaishi*, 1994, vol. 12, pp. 1081–1086.

Primary Examiner—Cynthia Hamilton
Attorney, Agent, or Firm—Ronald P. Kananen

[57] ABSTRACT

Disclosed are novel cyanoguanidine derivatives which are usable as an epoxy resin curing agent and are represented by the following general formula (1). A thermosetting resin composition and a photocurable and thermosetting resin composition containing the following cyanoguanidine derivatives and other derivatives as the epoxy resin curing agent are also disclosed.

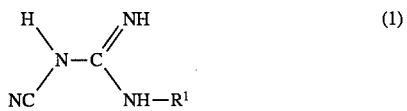

(1)

wherein $R^1$ represents a substituent selected from the group consisting of the following substituents (a) through (k).

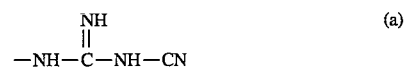

(a)

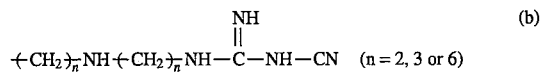

(b)

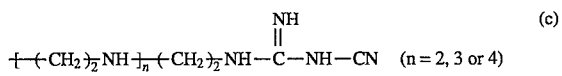

(c)

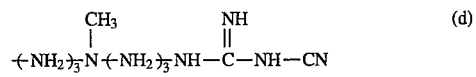

(d)

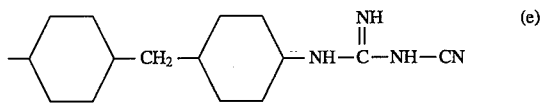

(e)

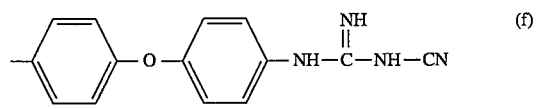

(f)

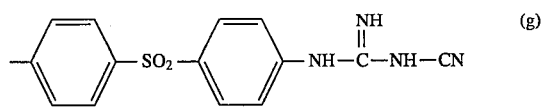

(g)

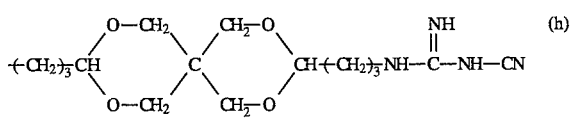

(h)

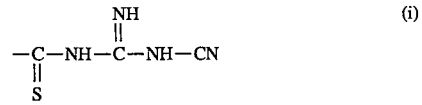

(i)

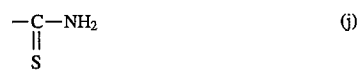

(j)

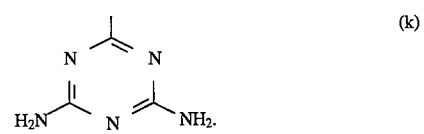

(k)

30 Claims, 7 Drawing Sheets

CYANOGUANIDINE DERIVATIVES, AND THERMOSETTING OR PHOTOCURABLE, THERMOSETTING RESIN COMPOSITION USING THE SAME

BACKGROUND OF THE INVENTION

1. Field of the Invention

This invention relates to novel cyanoguanidine derivatives and more particularly to novel cyanoguanidine derivatives which are advantageously usable in various applications such as, for example, an epoxy resin curing agent. This invention also relates to bis-cyanoguanidine type and cyanoguanidine type epoxy resin curing agents advantageously usable for hardening epoxy resins and to a thermosetting resin composition or a photocurable and thermosetting resin composition using the curing agent.

2. Description of the Prior Art

At the soldering step for mounting electronic parts as on the surface of a printed circuit board, the solder mask is used for the purpose of preventing the solder from adhering to impertinent portions and protecting the circuits from the external environment.

In consequence of the increased density of printed circuits in the board and in association with the problem of environmental pollution, the practice of using an alkali development type photocurable and thermosetting resin composition as the material for the solder mask has been popularized. As for the photocurable and thermosetting resin composition developable with an alkali aqueous solution, Kamayachi et al. U.S. Pat. No. 5,009,982 issued on Apr. 23, 1991 discloses a photocurable and thermosetting resin composition containing a photosensitive resin which is obtained by the reaction of a saturated or unsaturated polybasic acid anhydride with a reaction product of a novolak type epoxy compound and an unsaturated monocarboxylic acid and published Japanese Patent Application, KOKAI (Early Publication) No. (hereinafter referred to briefly as "JP-A") 3-289656 discloses a liquid photoimageable solder resist developable with an alkali aqueous solution, which uses a photosensitive resin obtained by the reaction of acrylic acid with a copolymer of an alkyl (meth)acrylate and a glycidyl (meth)acrylate and the subsequent reaction of a polybasic acid anhydride with the resultant reaction product. The alkali development type photocurable and thermosetting resin composition, however, is generally at a disadvantage in lacking storage stability because it is liable to gain in viscosity and form gel with the elapse of time. It is, therefore, marketed generally in the form of a two-component package which consists of a main agent formed mainly of a photosensitive resin and a hardener formed mainly of a thermosetting component. The consumer is expected to mix the main agent with the hardener at the time he makes use of the composition.

Incidentally, in the solder resist, a coating film formed of the photocurable and thermosetting resin composition is exposed to light and developed to produce a prescribed resist pattern and the resist pattern is thermally set by postcuring.

The alkali development type photocurable and thermosetting resin composition mentioned above is so adapted as to produce a solder resist film excelling in adhesiveness, hardness, resistance to heat, electrical insulation properties, or the like by using an epoxy resin, in general, as the thermosetting component and, during the course of the postcuring mentioned above, causing a copolymerization reaction between the carboxyl group in the side chain of the photosensitive resin and the epoxy group in the epoxy resin, in addition to the curing reaction of the thermosetting components. For the purpose of accelerating the reactions mentioned above during the course of the postcuring, an epoxy resin curing agent is generally used in combination with the epoxy resin.

Various compounds have been known as effective curing agents for epoxy resins. Cyanoguanidine (otherwise called "dicyandiamide") is well known as one of the curing agents. If cyanoguanidine is used in combination with an epoxy resin in the alkali development type photocurable and thermosetting resin composition, the mixture of the main agent with the hardener will be at a disadvantage in lacking storage stability and suffering from a short shelf life as a single liquid composition.

It is disclosed in International Publication WO 92/01726 that a substituted cyanoguanidine is useful as a curing agent for an epoxy resin. The invention disclosed in WO 92/01726 proposes to incorporate a specific substituent into cyanoguanidine for the purpose of improving the solubility thereof. Thus, it aims to provide a substituted cyanoguanidine compound which is soluble in various organic solvents.

Generally, a substituted cyanoguanidine compound which exhibits solubility in various organic solvents, however, readily reacts with an epoxy resin at normal room temperature because it also exhibits solubility in a liquid epoxy resin or in an epoxy resin solution. As a result, the photocurable and thermosetting resin composition which contains this substituted cyanoguanidine compound in combination with an epoxy resin has a short shelf life and is deficient in the potential curing property.

Redmon et al. U.S. Pat. No. 2,455,807 issued on Dec. 7, 1948 discloses substituted 3-cyanoguanidines which have aliphatic, aromatic, and heterocyclic substituents. They are claimed to be useful for the preparation of medicines, dyes, insecticides, antioxidants, vulcanization accelerators, plasticizers, resin modifiers, ion-exchange resins, and leather, paper, and textile processing agents. Their use as an epoxy resin curing agent is mentioned nowhere therein.

Compounds which resemble the cyanoguanidine derivatives of the present invention are disclosed in Journal of the Chemical Society, 1956, pp. 4422–4425 and JP-A-64-71, 846. Particularly, JP-A-64-71,846 discloses 1,6-di($N^3$-cyano-$N^1$-guanidino)hexane which is an intermediate useful for the production of bisbiguanidine and polybiguanidine to be used as disinfectants and biocides and chlorohexidine to be used as anti-fungus agents and antiseptics. The novel cyanoguanidine derivatives which the present invention aims to propose are mentioned nowhere in these publications. Neither is the use of the cyanoguanidine derivatives as an epoxy resin curing agent mentioned anywhere therein.

SUMMARY OF THE INVENTION

An object of the present invention, therefore, is to provide novel cyanoguanidine derivatives which are useful as an epoxy resin curing agent and also usable as an intermediate for other useful compounds.

Another object of the present invention is to provide an epoxy resin curing agent which is only sparingly soluble in various organic solvents and which possesses the so-called potential thermal reactivity, i.e. the ability to avoid reacting with an epoxy compound at low temperatures in the neighborhood of normal room temperature and react quickly therewith by the application of heat.

Still another object of the present invention is to provide a thermosetting resin composition which not only enjoys a long pot life but also excels in the so-called potential curing property, i.e. the ability to remain stable at low temperatures in the neighborhood of normal room temperature and cure quickly at high temperatures.

Yet another object of the present invention is to provide an alkali development type photocurable and thermosetting resin composition which excels in the photocuring property, the developability with an alkali aqueous solution, and the potential curing property and, at the same time, enjoys a long shelf life.

More specifically, the present invention has for its object the provision of an alkali development type photocuring and thermosetting resin composition which contains an epoxy resin curing agent possessing such potential thermal reactivity as mentioned above and, therefore, excels in storage stability, enjoys a long shelf life as a single liquid composition, and permits production of a cured coating film excelling in various properties such as adhesiveness, resistance to heat, resistance to chemicals, hardness, and electrical insulating properties which a solder resist is normally required to manifest.

To accomplish the objects described above, in accordance with one aspect of the present invention, there is provided a novel cyanoguanidine derivative represented by the following general formula (1):

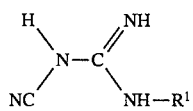  (1)

wherein R$^1$ represents a substituent selected from the group consisting of the following substituents (a) through (k).

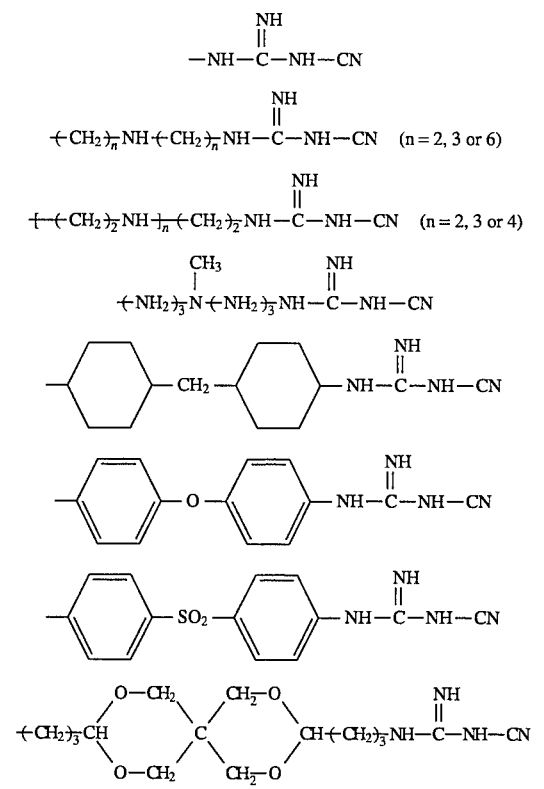

In accordance with another aspect of the present invention, there is provided an epoxy resin curing agent represented by the following general formula (1a):

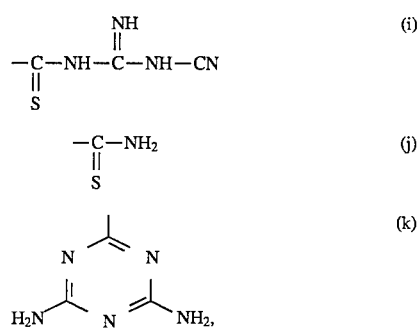  (1a)

wherein R$^2$ represents a substituent selected from the group consisting of the following substituents (1) through (35).

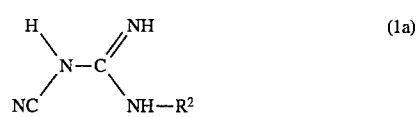  (1)

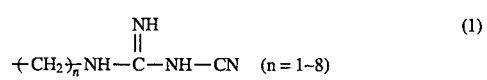  (2)

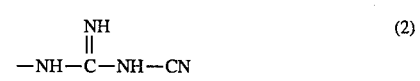  (3)

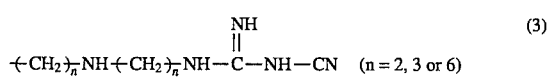  (4)

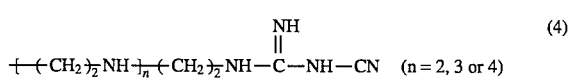  (5)

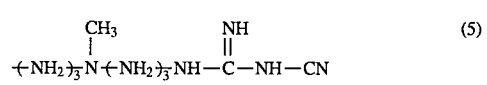  (6)

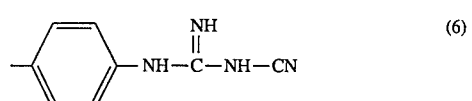  (7)

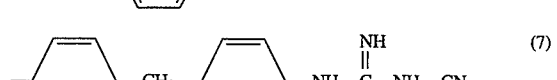  (8)

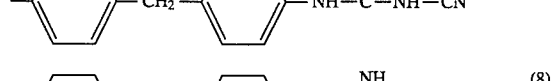  (9)

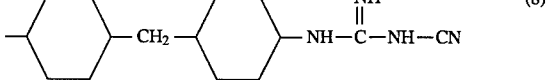  (10)

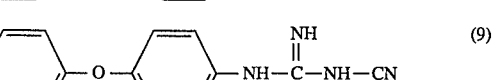

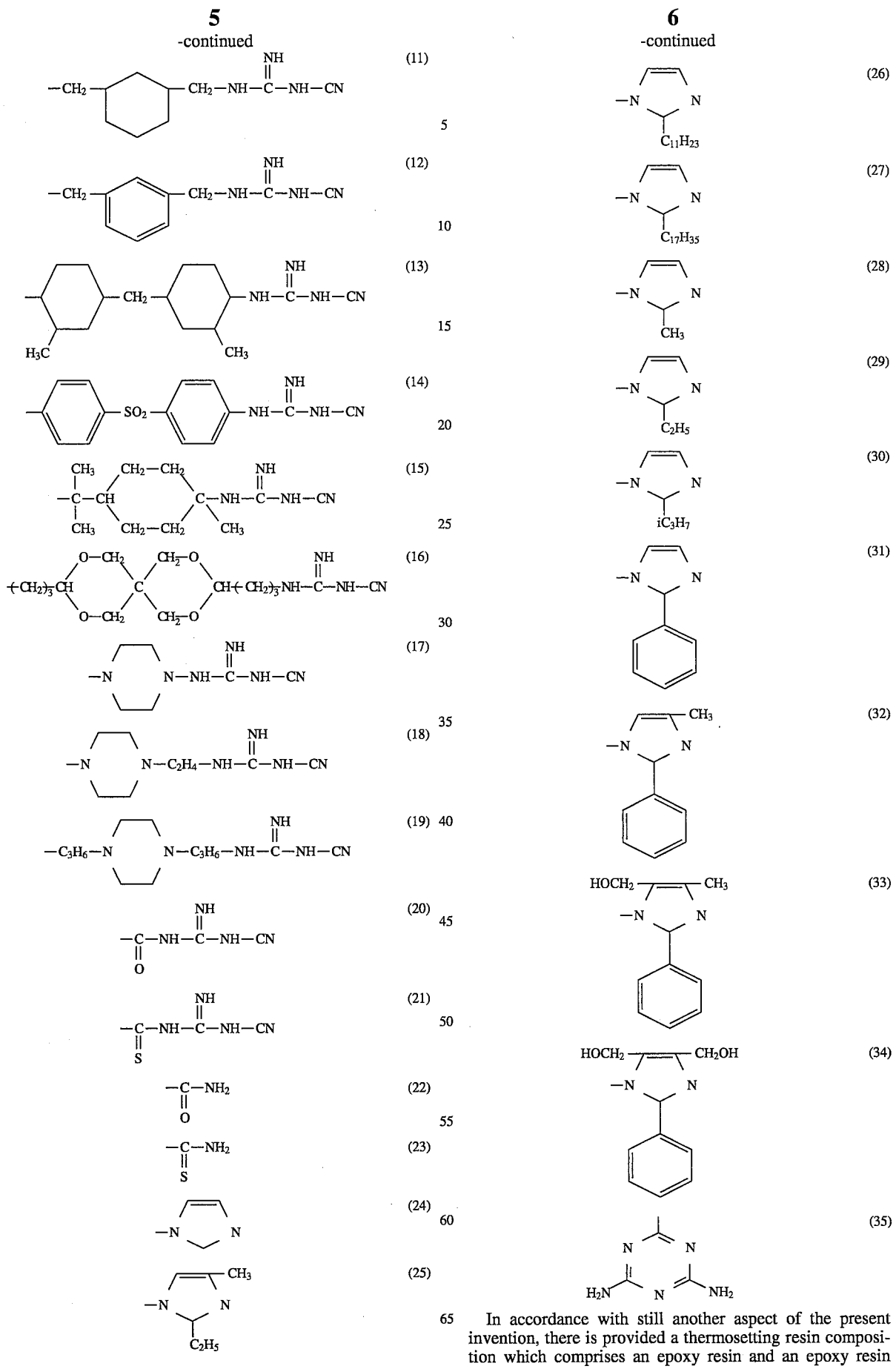
In accordance with still another aspect of the present invention, there is provided a thermosetting resin composition which comprises an epoxy resin and an epoxy resin curing agent represented by the general formula (1a) mentioned above.

In accordance with yet another aspect of the present invention, there is provided a photocuring and thermosetting resin composition which comprises (A) a resin curable by an active energy radiation, which has at least two ethylenically unsaturated bonds in combination with a carboxyl group in the molecular unit thereof, (B) a photopolymerization initiator, (C) a diluent, (D) an epoxy resin, and (E) an epoxy resin curing agent, the epoxy resin curing agent (E) being a cyanoguanidine derivative represented by the following general formula (1b).

$$\begin{array}{c} H \\ \diagdown \\ N-C \\ \diagup \quad \diagdown \\ NC \quad NH-R^3 \end{array} \begin{array}{c} NH \\ \| \end{array} \qquad (1b)$$

wherein $R^3$ represents a substituent selected from the group consisting of the following substituents (1) through (34).

$$\pm CH_2\pm_n NH-\overset{NH}{\underset{\|}{C}}-NH-CN \quad (n=1\sim 8) \qquad (1)$$

$$\pm CH_2\pm_n NH\pm CH_2\pm_n NH-\overset{NH}{\underset{\|}{C}}-NH-CN \quad (n=2, 3 \text{ or } 6) \qquad (2)$$

$$\pm\pm CH_2\pm_2 NH\pm_n\pm CH_2\pm_2 NH-\overset{NH}{\underset{\|}{C}}-NH-CN \quad (n=2, 3 \text{ or } 4) \qquad (3)$$

$$\pm NH_2\pm_3 N\pm NH_2\pm_3 NH-\overset{NH}{\underset{\|}{C}}-NH-CN \qquad (4)$$

(with $CH_3$ substituent on N)

(5) phenyl-NH-C(=NH)-NH-CN (6) phenyl-CH₂-phenyl-NH-C(=NH)-NH-CN (7) cyclohexyl-CH₂-cyclohexyl-NH-C(=NH)-NH-CN (8) phenyl-O-phenyl-NH-C(=NH)-NH-CN (9) 3,3,5-trimethylcyclohexyl-CH₂-NH-C(=NH)-NH-CN

(10) -CH₂-cyclohexyl-CH₂-NH-C(=NH)-NH-CN

(11) -CH₂-phenyl-CH₂-NH-C(=NH)-NH-CN

(12) dimethylcyclohexyl-CH₂-cyclohexyl-NH-C(=NH)-NH-CN

(13) phenyl-SO₂-phenyl-NH-C(=NH)-NH-CN

(14) trimethyl-cyclohexyl-C-NH-C(=NH)-NH-CN

(15) pentaerythritol-based: $+CH_2 +_3 CH$ ... $CH + CH_2 +_3 NH-C(=NH)-NH-CN$

(16) piperazinyl -N(CH₂CH₂)₂N-NH-C(=NH)-NH-CN

(17) -N(CH₂CH₂)₂N-C₂H₄-NH-C(=NH)-NH-CN

(18) -C₃H₆-N(CH₂CH₂)₂N-C₃H₆-NH-C(=NH)-NH-CN

(19) -C(=O)-NH-C(=NH)-NH-CN

(20) -C(=S)-NH-C(=NH)-NH-CN

(21) -C(=O)-NH₂

(22) -C(=S)-NH₂

(23) imidazolyl -N⟨⟩N

(24) -N⟨⟩N-CH₃ (with C₂H₅)

(25) -N⟨⟩N (with C₁₁H₂₃)

(26) -N⟨⟩N (with C₁₇H₃₅)

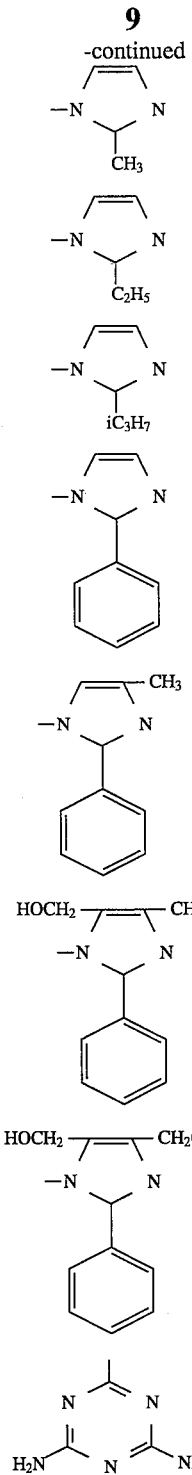

(27), (28), (29), (30), (31), (32), (33), (34)

BRIEF DESCRIPTION OF THE DRAWINGS

Other objects, features, and advantages of the invention will become apparent from the following description taken together with the drawings, in which.

DETAILED DESCRIPTION OF THE INVENTION

Figure 1:
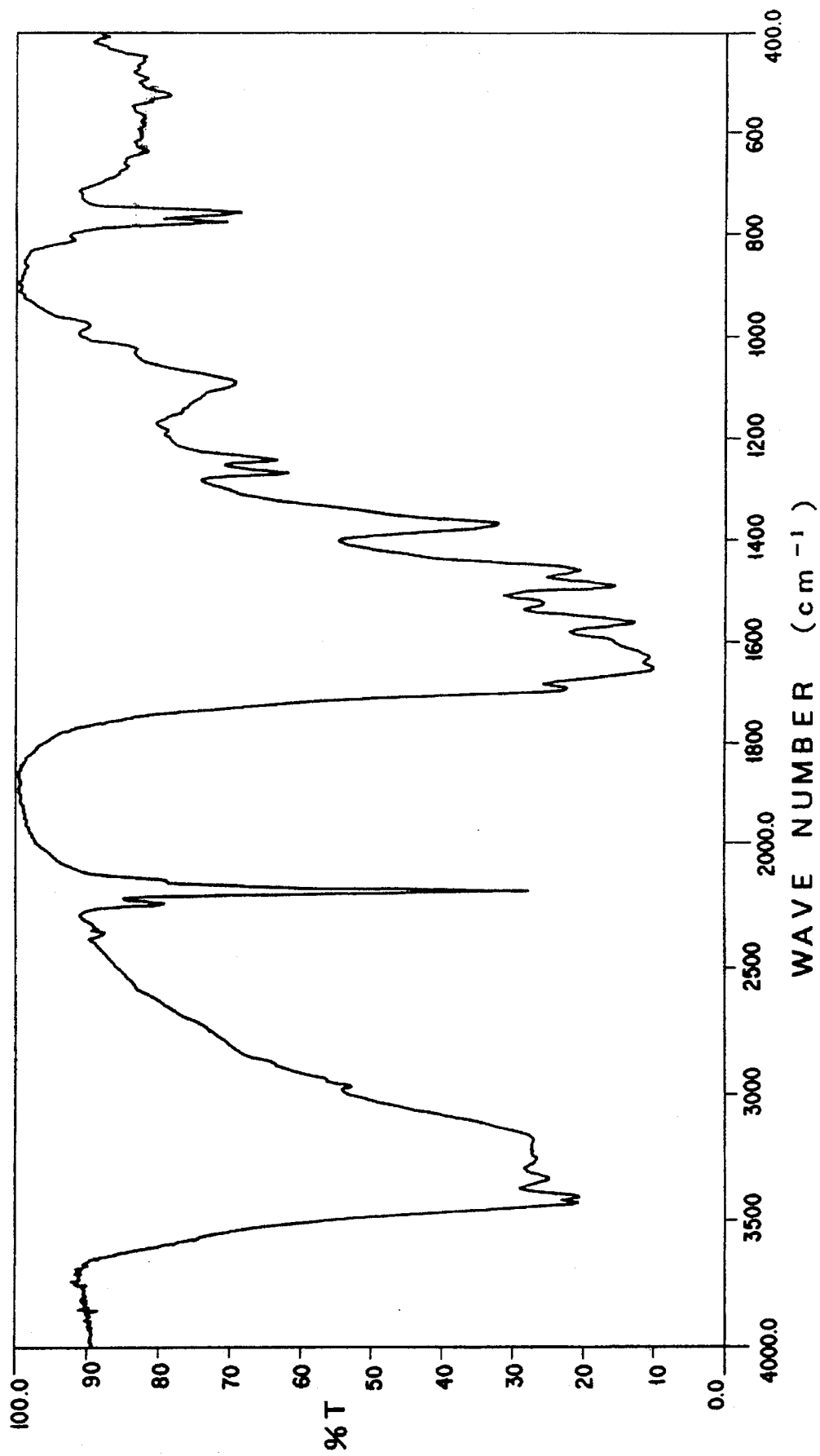
FIG. 1 shows an IR (infrared absorption) spectrum of 1,1-bis(3-cyanoguanidine) obtained in Synthesis Example 1.

The invention published in WO 92/01726, as remarked above, proposes the incorporation of a specific substituent in cyanoguanidine for the purpose of improving the solubility of the compound.

The present invention, utterly unlike the conventional approach of this kind, contemplates incorporating a specific substituent into cyanoguanidine thereby rendering the resultant cyanoguanidine derivative sparingly soluble in organic solvents, imparting improved potential thermal reactivity thereto, and enabling the specific substituent (functional group) contained therein to manifest the characteristic properties thereof.

The cyanoguanidine derivative of the present invention can be advantageously manufactured by the method of F. L. Rose and G. Swain (reported in J. Chem. Soc., 1956, pp. 4422–4425 mentioned above) and the method disclosed in JP-A-64-71,846.

Specifically, when an alkali dicyanamide such as, for example, sodium dicyanamide and a salt of an amine compound having a substituent R, preferably a hydrochloride thereof, are heated in a suitable solvent under reflux, they react in accordance with the following formula (2) to produce the cyanoguanidine derivative as aimed at.

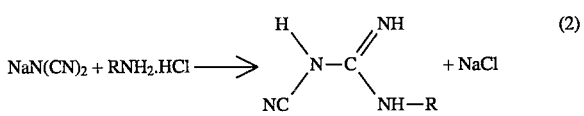

(2)

In the cyanoguanidine derivatives according to the present invention which are represented by the general formula (1a) mentioned above, the bis-cyanoguanidine type derivatives having substituents $R^2$ of the formulas (1) through (21) are synthesized desirably in accordance with the following reaction formula (3). Specifically, when an alkali dicyanamide such as, for example, sodium dicyanamide and a salt of a diamine compound having a substituent $R^4$, preferably a dihydrochloride thereof, are heated in a suitable solvent under reflux, they react in accordance with the following formula (3) to produce the bis-cyanoguanidine type derivative as aimed at.

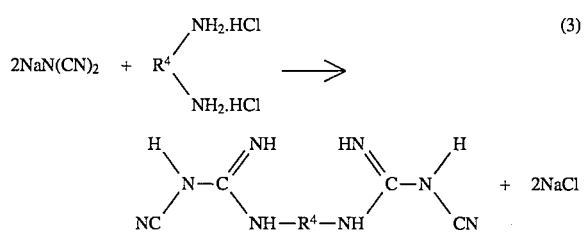

$$2NaN(CN)_2 + R^4 \begin{matrix} NH_2 \cdot HCl \\ NH_2 \cdot HCl \end{matrix} \longrightarrow \quad (3)$$

In the reaction formula (3), the substituent $R^4$ means the residue which arises from the removal of a cyanoguanidyl group from the substituent $R^2$.

In either of the reactions described above, the relevant reactants may be incorporated in practically stoichiometric proportions in the solvent. As the reaction solvent, water and alcohols having 1 to 6 carbon atoms, preferably 3 to 5 carbon atoms such as butanol, propanol, and ethanol, particularly desirably n-butanol, and mixtures of such alcohols with water may be used. It is also permissible to use such neutral solvents as dimethyl formamide and sulforan.

When water is used as the solvent, the reaction can be accelerated by the presence of a catalytic amount of a base. As the base, aliphatic or alicyclic amines and N-heterocyclic bases such as triethyl amine, N-methyl morpholine, and pyridine may be used. The pH of the reaction mixture at the start of the reaction is desired to be adjusted on an alkali side, preferably in the range of 8 to 10, from the viewpoint of yield. This pH adjustment can be effected by the amount of the base to be added to the reaction mixture.

The reaction is carried out by refluxing the reaction mixture at a temperature in the approximate range of from 75° C. to 170° C., preferably from 90° C. to 160° C., generally in a stirred state for a period in the range of from 3 to 16 hours, preferably 6 to 10 hours, depending on the temperature of heating. After the reaction is completed, the reaction solution is distilled, when necessary, to expel the solvent and then washed with water, a mixture of water and alcohol, or a mixture of water and acetone to clean the alkali salt (NaCl) and, at the same time, induce crystallization of the reaction product. The reaction product is separated by filtration from the salt-containing liquid phase. The separated solid is dried to obtain a finished product. The drying is desired to be effected by heating in a vacuum.

In accordance with one aspect of the present invention, there are provided novel cyanoguanidine derivatives represented by the general formula (1) mentioned above. A few of these novel cyanoguanidine derivatives will be cited below by way of example and the processes used for their synthesis will be specifically described below.

SYNTHESIS EXAMPLE 1

Synthesis of 1,1-bis(3-cyanoguanidine)

The reaction of sodium dicyanamide with hydrazine dihydrochloride proceeds as shown by the following formula (4) to produce 1,1-bis(3-cyanoguanidine) as aimed at.

$$2NaN(CN)_2 + H_2N.NH_2.2HCl \longrightarrow \quad (4)$$

-continued

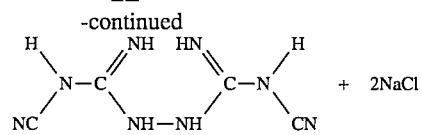

This synthesis was specifically carried out in accordance with the following procedure.

In an eggplant type flask having an inner volume of 100 ml and equipped with a Dimroth condenser, 8.90 g (0.10 mol) of sodium dicyanamide (produced by Aldrich Corp.), 5.25 g (0.05 mol) of hydrazine dihydrochloride, 50 ml of water, and 0.02 g of triethylamine were charged. Then, the flask containing the reactants was placed in an oil bath and the reactants were stirred with a magnetic stirrer under a refluxed condition and thus left reacting for 5 hours at about 100° C.

After the reaction was completed, the reaction solution was distilled under a reduced pressure in an evaporator to expel the reaction solvent. The residue of the distillation and a mixture of water/methanol (mixing ratio of 2.5/1.5) added thereto were mixed thoroughly. The resultant mixture was passed through a glass filter. The solid consequently separated was dried in a vacuum drier at 80° C. for 8 hours, to obtain 3.9 g of light red 1,1-bis(3-cyanoguanidine) (yield 47.7%).

The resultant product, 1,1-bis(3-cyanoguanidine) (hereinafter referred to briefly as "2CG"), was analyzed by the use of a Fourier-transform spectrophotometer, FT-IR, to obtain an IR spectrum which is shown in FIG. 1. It is clearly noted from this spectrum that the peak due to the C-N stretching vibration of the cyanoguanidyl group of 2CG appears at a wave number of 1250 cm$^{-1}$, that due to the C=N stretching vibration at a wave number of 1651 cm$^{-1}$, and that due to the C≡N stretching vibration at a wave number of 2190 cm$^{-1}$.

Figure 2:
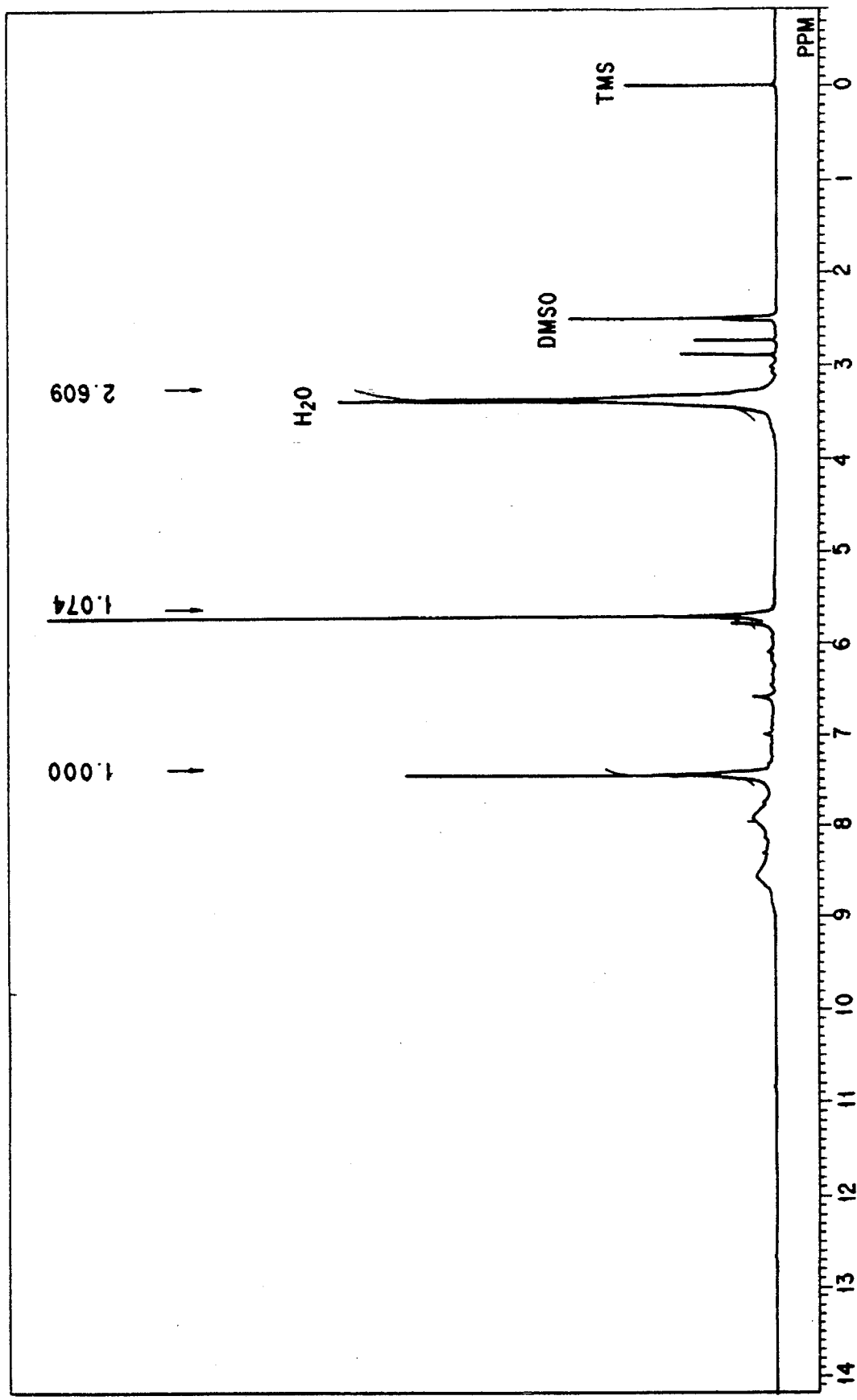
FIG. 2 shows a $^1$H-NMR (nuclear magnetic resonance) spectrum of 1,1-bis(3-cyanoguanidine) obtained in Synthesis Example 1.

The $^1$H-NMR spectrum [solvent DMSO (dimethyl sulfoxide) and the internal standard TMS (tetramethyl silane)] of 2CG is shown in FIG. 2. The curve showing the proton integral ratio of each peak is additionally shown in FIG. 2.

SYNTHESIS EXAMPLE 2

Synthesis of 3,9-bis(3-cyanoguanidinopropyl)-2,4,8,10-tetraoxaspiro[5.5]undecane The reaction of sodium dicyanamide with 3,9-bis(3-aminopropyl)-2,4,8,10-tetraoxaspiro[5.5]undecane dihydrochloride proceeds as shown by the following formula (5) to produce 3,9-bis(3-cyanoguanidinopropyl)-2,4,8,10-tetraoxaspiro[5.5]undecane aimed at.

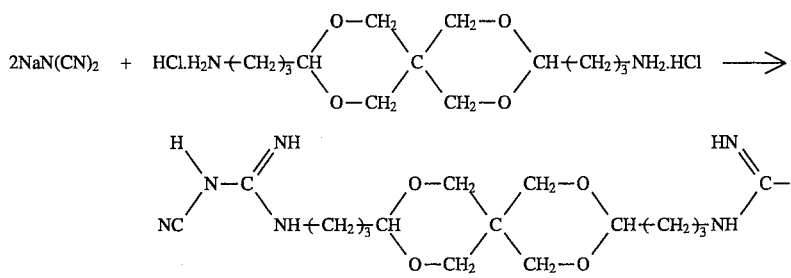

(5)

This synthesis was carried out in accordance with the following procedure.

In an eggplant type flask having an inner volume of 50 ml and equipped with a Dimroth condenser, 0.89 g (0.01 mol) of sodium dicyanamide, 1.74 g (0.005 mol) of 3,9-bis(3-aminopropyl)-2,4,8,10-tetraoxaspiro[5.5]undecane dihydrochloride, and 10 ml of n-butanol were charged. Then, the flask containing the reactants was placed in an oil bath and the reactants were stirred with a magnetic stirrer under a refluxed condition and thus left reacting for 8 hours at about 118° C.

The reaction solution was after-treated by following the procedure of Synthesis Example 1, to obtain 1.99 g of 3,9-bis(3-cyanoguanidinopropyl)-2,4,8,10-tetraoxaspiro[5.5]undecane (yield 97.5%).

Figure 3:
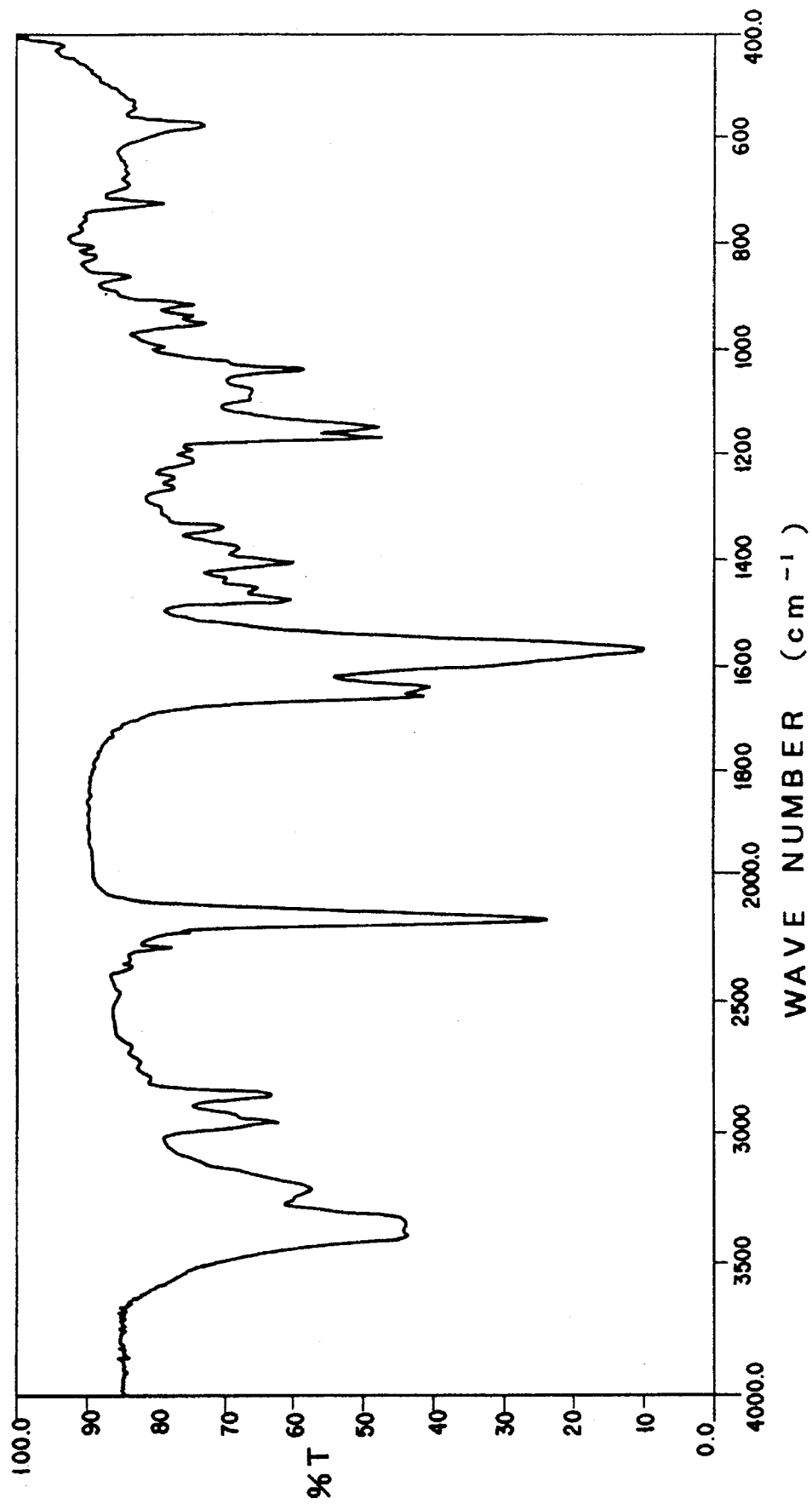
FIG. 3 shows an IR spectrum of 3,9-bis(3-cyanoguanidinopropyl)-2,4,8,10-tetraoxaspiro[5.5]undecane obtained in Synthesis Example 2.

The resultant product, 3,9-bis(3-cyanoguanidinopropyl)-2,4,8,10-tetraoxaspiro[5.5]undecane (hereinafter referred to briefly as "ATU2CG") was analyzed by the use of a Fourier-transform spectrophotometer, FT-IR, to obtain an IR spectrum which is shown in FIG. 3. It is clearly noted from this spectrum that the peak due to the C=N stretching vibration of the cyanoguanidyl group of ATU2CG appears at a wave number of 1656 cm$^{-1}$ and that due to the C≡N stretching vibration at a wave number of 2176 cm$^{-1}$.

Figure 4:
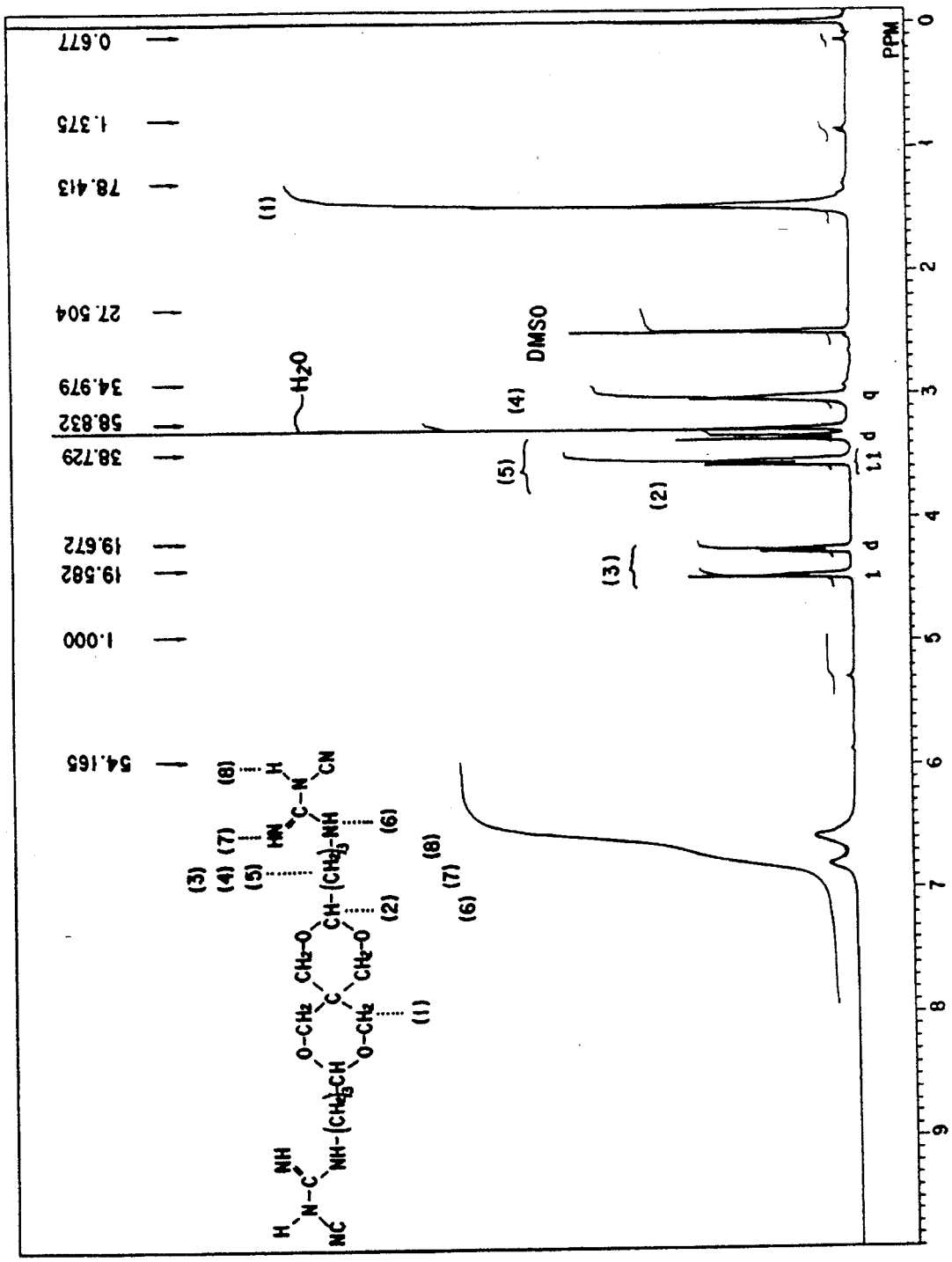
FIG. 4 shows a $^1$H-NMR spectrum of 3,9-bis(3-cyanoguanidinopropyl)-2,4,8,10-tetraoxaspiro[5.5]undecane obtained in Synthesis Example 2.

The $^1$H-NMR spectrum (solvent DMSO and the internal standard TMS) of ATU2CG is shown in FIG. 4. The curve showing the proton integral ratio of each peak is additionally shown in FIG. 4. In the diagram, the symbols (1) through (8) denote the symbols of the hydrogen atoms linked to the carbon atoms of the ATU2CG.

SYNTHESIS EXAMPLE 3

Synthesis of 2-cyanoguanidyl-4,6-diamino-S-triazine

The reaction of sodium dicyanamide with 2,4,6-triamino-S-triazine hydrochloride proceeds as shown by the following formula (6) to produce 2-cyanoguanidyl-4,6-diamino-S-triazine as aimed at.

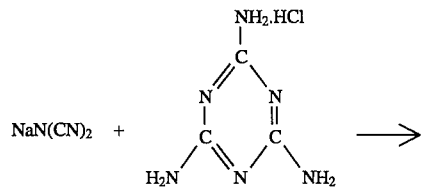

(6)

-continued

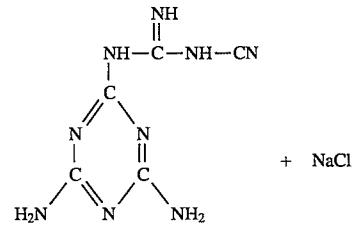

+ NaCl

This synthesis was carried out in accordance with the following procedure.

In an eggplant type flask having an inner volume of 100 ml and equipped with a Dimroth condenser, 8.9 g (0.10 mol) of sodium dicyanamide, 1.63 g (0.10 mol) of 2,4,6-triamino-S-triazine hydrochloride, and 20 ml of n-butanol were charged. Then, the flask containing the reactants was placed in an oil bath and the reactants were stirred with a magnetic stirrer under a refluxed condition and thus left reacting for 5 hours at about 118° C.

After the reaction was completed, the reaction solution was distilled under a reduced pressure in an evaporator to expel the reaction solvent. The residue of the distillation and a mixture of water/acetone (mixing ratio of 1.0/1.0) added thereto were mixed thoroughly. The resultant mixture was passed through a glass filter. The solid consequently separated was dried in a vacuum drier at 80° C. for 8 hours, to obtain 0.55 g of white 2-cyanoguanidyl-4,6-diamino-S-triazine (yield 28.5%).

Figure 5:
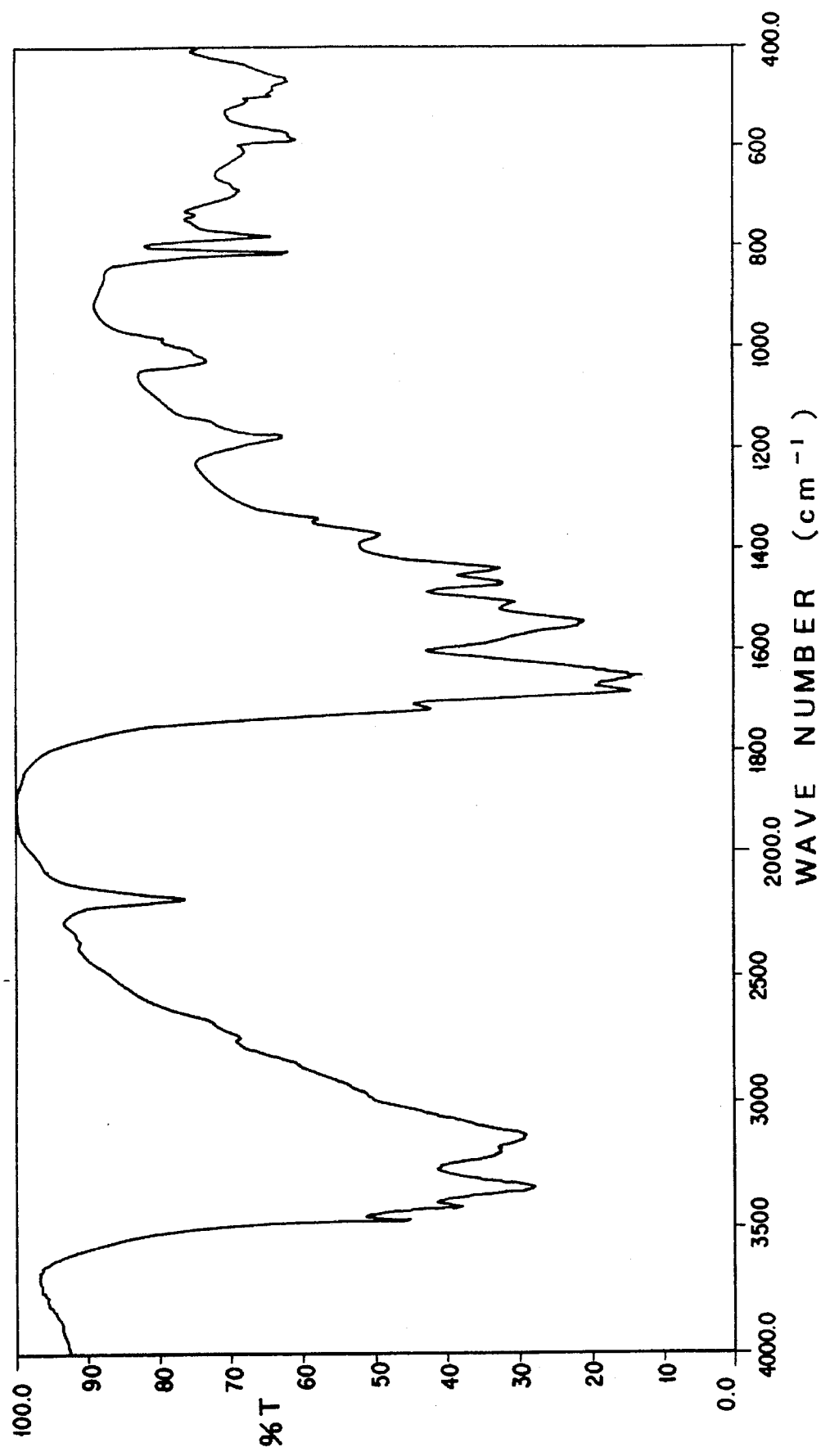
FIG. 5 shows an IR spectrum of 2-cyanoguanidyl-4,6-diamino-S-triazine obtained in Synthesis Example 3.

The resultant product, 2-cyanoguanidyl-4,6-diamino-S-triazine (hereinafter referred to briefly as "MD"), was analyzed by the use of a Fourier-transform spectrophotometer, FT-IR, to obtain an IR spectrum which is shown in FIG. 5. It is clearly noted from this Spectrum that the peak due to the C≡N stretching vibration of the cyanoguanidyl group of MD appears at a wave number of 2195 cm$^{-1}$.

Figure 6:
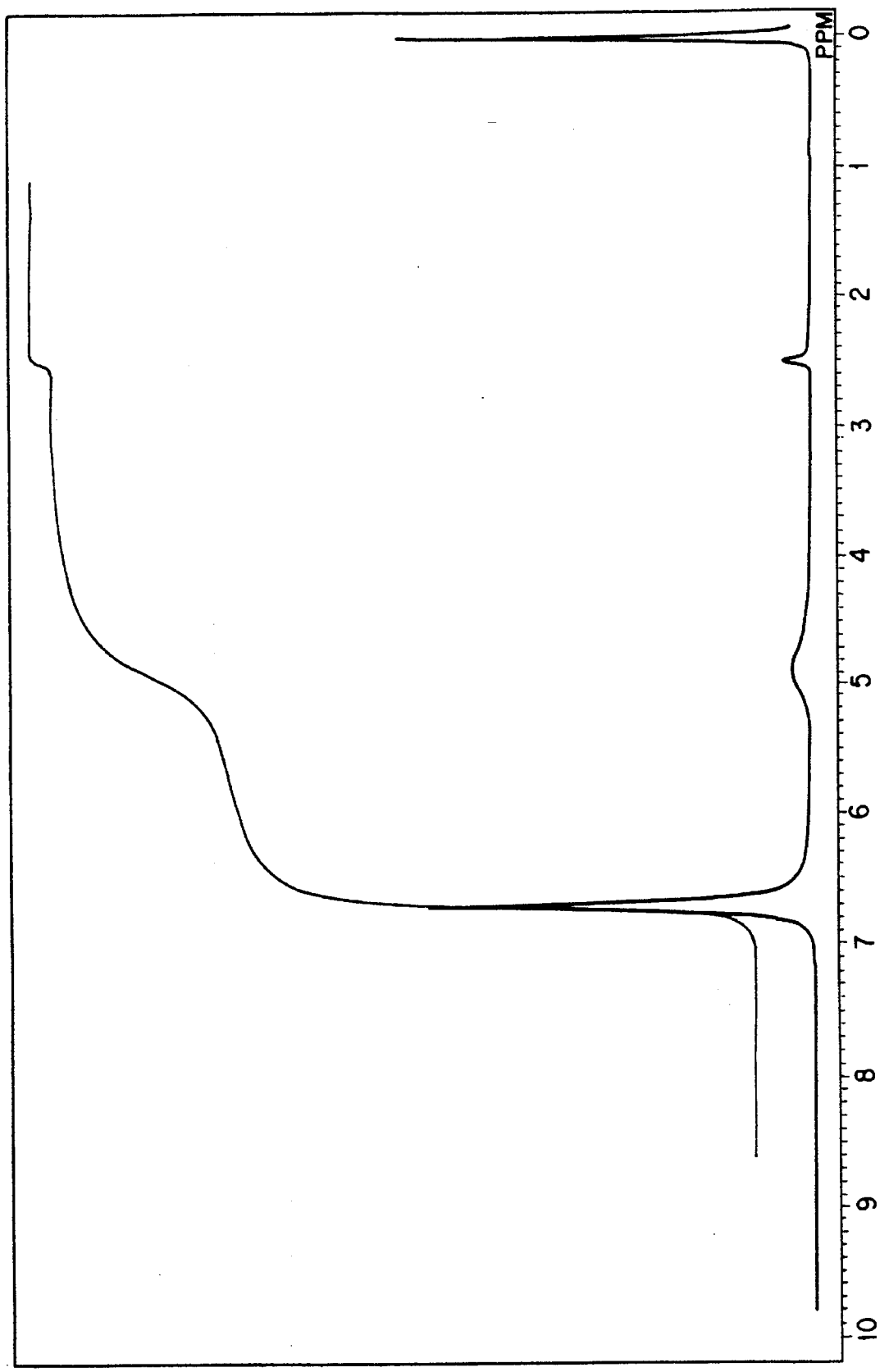
FIG. 6 shows a $^1$H-NMR spectrum of 2-cyanoguanidyl-4,6-diamino-S-triazine obtained in Synthesis Example 3.

The $^1$H-NMR spectrum (solvent DMSO and the internal standard TMS) of MD is shown in FIG. 6. The curve showing the proton integral ratio of the peaks is additionally shown in FIG. 6.

Synthesis examples of some other cyanoguanidine derivatives which may be advantageously used in the thermosetting resin composition and the photocurable and thermosetting resin composition will be specifically described below.

SYNTHESIS EXAMPLE 4

Synthesis of 1,1'-p-phenylene-bis-3,3'-cyanoguanidine

The reaction of sodium dicyanamide with p-phenylenediamine dihydrochloride proceeds as shown by the following formula (7) to produce 1,1'-p-phenylene-bis-3,3'-cyanoguanidine as aimed at.

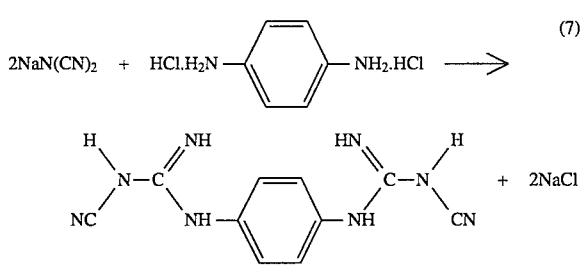

(7)

This synthesis was carried out in accordance with the following procedure.

In an eggplant type flask having an inner volume of 50 ml and equipped with a Dimroth Condenser, 0.89 g (0.01 mol) of sodium dicyanamide, 0.91 g (0.005 mol) of p-phenylenediamine dihydrochloride, 10 ml of n-butanol were charged. Then, the flask containing the reactants was placed in an oil bath and the reactants were stirred with a magnetic stirrer under a refluxed condition and thus left reacting for 8 hours at about 118° C.

After the reaction was completed, the reaction solution was distilled under a reduced pressure in an evaporator to expel the reaction solvent. The residue of the distillation and a mixture of water/methanol (mixing ratio of 2.5/1.5) added thereto were mixed thoroughly. The resultant mixture was passed through a glass filter. The solid consequently separated was dried in a vacuum drier at 80° C. for 8 hours, to obtain 0.98 g (yield 81.3%) of light gray 1,1'-p-phenylene-bis-3,3'-cyanoguanidine (hereinafter referred to briefly as "Ph2CG").

SYNTHESIS EXAMPLE 5

Synthesis of methylene-bis(1,1'-p-phenylene-3,3'-cyanoguanidine)

The reaction of sodium dicyanamide with 4,4'-diaminodiphenylmethane dihydrochloride proceeds as shown by the following formula (8) to produce methylene-bis(1,1'-p-phenylene-3,3'-cyanoguanidine) as aimed at.

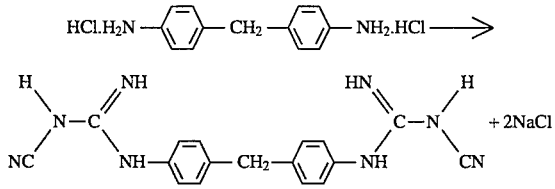

(8)

This synthesis was carried out in accordance with the following procedure.

In an eggplant type flask having an inner volume of 50 ml and equipped with a Dimroth condenser, 0.89 g (0.01 mol) of sodium dicyanamide, 1.37 g (0.005 mol) of 4,4'-diaminodiphenylmethane dihydrochloride, 10 ml of n-butanol were charged. Then, the flask containing the reactants was placed in an oil bath and the reactants were stirred with a magnetic stirrer under a refluxed condition and thus left reacting for 8 hours at about 118° C.

After the reaction was completed, the reaction solution was distilled under a reduced pressure in an evaporator to expel the reaction solvent. The residue of the distillation and a mixture of water/methanol (mixing ratio of 2.5/1.5) added thereto were mixed thoroughly. The resultant mixture was passed through a glass filter. The solid consequently separated was dried in a vacuum drier at 80° C. for 8 hours, to obtain 1.33 g (yield 80.1%) of yellow methylene-bis(1,1'-p-phenylene-3,3'-cyanoguanidine) (hereinafter referred to briefly as "DDM-2CG").

In the cyanoguanidine derivatives according to the present invention which are represented by the general formula (1a) mentioned above, the compounds having substituents $R^2$ of the formulas (1) through (21) are bis-cyanoguanidine type derivatives which have two cyanoguanidyl groups at the opposite terminals and, therefore, possess six active hydrogen atoms linked to the nitrogen atoms of the cyanoguanidyl groups. Theoretically, therefore, they can react with six epoxy groups. The compounds having substituents $R^2$ of the formulas (22) through (35) are cyanoguanidine derivatives having amine type substituents incorporated therein. They exhibit notably high basicity and abound in reactivity with epoxy compounds. Nevertheless, these cyanoguanidine derivatives are generally sparingly soluble in various organic solvents, liquid epoxy compounds, or epoxy compound solutions. They avoid reacting with an epoxy group at normal room temperature but react with an epoxy group by application of heat. Thus, they can be used particularly advantageously as a potentially themoreactive curing agent for epoxy resin.

By combining a cyanoguanidine derivative of the present invention possessing these characteristics with an epoxy compound, there is obtained a thermosetting resin composition which excels in the so-called latent or potential curing property, i.e. the property of remaining stably at low temperatures in the neighborhood of normal room temperature and quickly curing at high temperatures, and enjoys a long pot life as well. Further, the thermosetting resin composition permits production of a cured epoxy resin whose hardness may be varied from a relatively low hardness to high hardness depending on the substituent incorporated in the cyanoguanidine derivative.

In accordance with another aspect of the present invention, therefore, there is provided a thermosetting resin composition which comprises an epoxy resin and an epoxy resin curing agent represented by the general formula (1a) mentioned above.

As the epoxy resin to be contained in combination with the cyanoguanidine derivative mentioned above in the thermosetting resin composition of the present invention, any of the well-known epoxy resins (including epoxy oligomers) which has at least one epoxy group, preferably two or more epoxy groups in the molecular unit thereof may be used. As typical examples, the glycidyl ether type epoxy resins such as the bis-phenol A type epoxy resin obtained by the reaction of bis-phenol A with epichlorohydrin in the presence of an alkali, the epoxide of a resin resulting from the condensation of bis-phenol A with formalin, and the equivalent using bromated bis-phenol A in the place of bis-phenol A may be cited. Novolak type epoxy resins such as the phenol novolak type, orthocresol novolak type, and p-t-butyl phenol novolak type epoxy resins which are obtained by glycidyl-etherifying the corresponding novolak resins with epichlorohydrin may be also cited. Then, the bis-phenol F type and the bis-phenol S type epoxy resins obtained by the reaction of epichlorohydrin on bis-phenol F and bis-phenol S are other concrete examples. Further, alicyclic epoxy resins possessing a cyclohexene oxide group, a tricyclodecene oxide group, or a cyclopentene oxide group; glycidyl ester resins such as phthalic diglycidyl ester, tetrahydrophthalic diglycidyl ester, hexahydrophthalic diglycidyl ester, diglycidyl-p-oxybenzoic acid, and dimeric acid glycidyl ester; glycidyl amine type resins such as tetraglycidyl diamino-diphenyl methane, triglycidyl-p-aminophenol, diglycidyl aniline, diglycidyl toluidine, tetraglycidyl methaxylylene diamine, diglycidyl tribromoaniline, and tetraglycidyl bis-aminomethyl cyclohexane; hydantoin type epoxy resins having glycidyl groups linked to their hydantoin rings; triglycidyl (or tris(2,3-epoxypropyl)) isocyanurate possessing a triazine ring; bixylenol type epoxy resins; and biphenol type epoxy resins are other examples. The epoxy resins mentioned above may be used either singly or in the form of a combination of two or more members.

The mixing ratio of the cyanoguanidine derivative mentioned above to the epoxy resin can be suitably set. From the standpoint of the characteristic properties of the cured coating film, however, the mixing ratio is desired to be such that the proportion of hydrogen of the amino group in the cyanoguanidine derivative falls in the range of from 0.05 to 1.0 mol per one mol of the epoxy group of the epoxy resin.

The thermosetting resin composition of the present invention, when necessary, may incorporate therein any of well-known organic solvents. Examples of the organic solvents include, but are not limited to: ketones such as methylethyl ketone and cyclohexanone; aromatic hydrocarbons such as toluene, xylene, and Ipsol #150 (trademark for tetramethyl benzene-based petroleum solvent of Idemitsu Petrochemical Co., Ltd.); glycol ethers such as cellosolve, butyl cellosolve, carbitol, butyl carbitol, propylene glycol monomethyl ether, dipropylene glycol monomethyl ether; and acetates such as ethyl acetate, butyl acetate, cellosolve acetate, butyl cellosolve acetate, carbitol acetate, butyl carbitol acetate, propylene glycol monomethyl ether acetate, and dipropylene glycol monomethyl ether acetate. These organic solvents may be used either singly or in the form of a combination of two or more members.

The thermosetting resin composition according to the present invention begins to undergo a curing reaction at a temperature in the approximate range of from 100° C. to 250° C. The epoxy compound thereof in a liquid state or in the form of a molten liquid is consequently converted into an insoluble or infusible solid three-dimensionally cross-linked product and eventually obtained as a cured article resembling a film or a sheet like an adhesive agent layer in structure. When a molding treatment is simultaneously carried out with this curing treatment, the cured article is obtained in the form of a shaped article such as, for example, a cast article, a pressed article or a laminated article. Optionally the curing treatment may be implemented by a two-stage process in which the curing reaction is temporarily suspended halfway along the entire course of reaction. In this case, a curable precondensate (so-called B-stage) which is still in a fusible and soluble state is obtained. The precondensate of this quality can be stably stored for a long time and can be used for the production of prepregs and for the production of a compression molding composition and a sintering powder, for example.

The thermosetting resin composition according to the present invention can be advantageously used in various technical fields such as those involving surface protection techniques, lamination techniques, or the like and in various industrial fields as electrical industry and building industry. It may be used, for example, as adhesive agents, protective coating materials for printed circuit boards, insulating resin varnishes, paints, lacquers, compression molding resin compositions, casting resin compositions, injection molding compounds, impregnating resin compositions, laminating resin compositions, sealing and filling resin compositions, and floor finishing resin compositions.

The present inventor has further ascertained by their study that when an alkali development type photocurable and thermosetting resin composition is produced by incorporating therein a cyanoguanidine derivative represented by the general formula (1b) mentioned above as an epoxy resin curing agent, this resin composition exhibits excellent storage stability, enjoys a long shelf life as a single liquid composition, and permits production of a cured coating film which excels in such properties as adhesiveness, resistance to heat, resistance to chemicals, hardness, and electrical insulating properties which a solder resist is required to possess.

Thus, in yet another aspect of the present invention, there is provided a photocurable and thermosetting resin composition which comprises (A) a resin curable by an active energy radiation (hereinafter referred to briefly as "radiation-curable resin") which has at least two ethylenically unsaturated bonds in combination with a carboxyl group in the molecular unit thereof, (B) a photopolymerization initiator or photosensitizer, (C) a diluent, (D) an epoxy resin, and (E) an epoxy resin curing agent, the epoxy resin curing agent (E) being a cyanoguanidine derivative represented by the general formula (1b) mentioned above.

Since the photocurable and thermosetting resin composition of the present invention contains the specific cyanoguanidine derivative mentioned above as the epoxy resin curing agent, it excels in storage stability, enjoys a long shelf life as a single liquid composition, and therefore augments the adaptability of the work for the manufacture of a solder resist film.

As the radiation-curable resin (A) mentioned above which has in combination at least two ethylenically unsaturated bonds and a carboxyl group in the molecular unit thereof, (1) the product obtained by the esterification of the epoxy group of a polyfunctional novolak type epoxy resin with the carboxyl group of an unsaturated monocarboxylic acid and the subsequent reaction of a saturated or unsaturated polybasic acid anhydride with the resultant hydroxyl group, (2) the product obtained by the reaction of (meth)acrylic acid with a copolymer composed of an alkyl (meth)acrylate and a glycidyl (meth)acrylate and the subsequent reaction of a saturated or unsaturated polybasic acid anhydride with the resultant reaction product, (3) the product obtained by the reaction of (meth)acrylic acid with a copolymer composed of a hydroxyalkyl (meth)acrylate, an alkyl (meth)acrylate, and a glycidyl (meth)acrylate and the subsequent reaction of a saturated or unsaturated polybasic acid anhydride with the resultant product, and (4) the product obtained by the partial reaction of a glycidyl (meth)acrylate with a copolymer composed of an alkyl (meth)acrylate and (meth)acrylic acid can be used, for example.

Since the radiation-curable resin mentioned above has numerous free carboxyl groups added to the side chain of a backbone polymer, the composition containing this resin is developable with a dilute aqueous alkali solution. When the applied coating film of the composition is developed after exposure to light and then postcured, the epoxy group of the epoxy resin separately added to the composition as a thermosetting component copolymerizes with the free carboxyl groups in the side chain of the radiation-curable resin mentioned above and converts the coating film into a solder resist film excellent in such properties as heat resistance, solvent resistance, acid resistance, adhesiveness, electrical properties, and hardness.

The acid value of the radiation-curable resin mentioned above should be in the range of from 40 to 160 mg KOH/g.

Preferably, this acid value is from 50 to 140 mg KOH/g in the resin (1), from 50 to 150 mg KOH/g in the resins (2) and (4), and from 40 to 120 mg KOH/g in the resin (3) mentioned above. Any deviation of the acid value from the aforementioned range is undesirable because the resin will manifest insufficient solubility in an aqueous alkali solution if the acid value is less than 40 mg KOH/g. Conversely, the acid value exceeding 160 mg KOH/g will give cause to deteriorate the various properties of the cured film such as resistance to alkalis and electrical properties expected of a resist.

The resin (1) mentioned above is obtained by causing the product of the reaction of such a novolak type epoxy resin as will be specifically described hereinafter with an unsaturated monocarboxylic acid to react with such a dibasic acid anhydride as phthalic anhydride or such an aromatic polycarboxylic anhydride as trimellitic anhydride or pyromellitic anhydride. In this case, the resin obtained by the reaction of at least 0.15 mol of a polybacic acid anhydride with each of the hydroxyl groups possessed by the reaction product of the novolak type epoxy resin with an unsaturated monocarboxylic acid proves to be suitable. When the number of ethylenically unsaturated bonds present in the molecular unit of the resin is small, the produced composition has a low speed of photocuring. It is therefore desired to use a novolak type epoxy resin as the raw material. A bisphenol A type epoxy resin may be used in combination therewith for the purpose of lowering the viscosity of the ink.

Typical examples of the novolak type epoxy resins include phenol novolak type epoxy resins, cresol novolak type epoxy resins and novolak type epoxy resins of bisphenol A. The resins which are obtained by causing epichlorohydrin to react with the corresponding novolak resins by the conventional method may be effectively used.

Examples of the unsaturated monocarboxylic acids mentioned above include, but are not limited to: acrylic acid, methacrylic acid, cinnamic acid, and the reaction product of a saturated or unsaturated dibasic acid anhydride with a (meth)acrylate having one hydroxyl group per molecule. These unsaturated monocarboxylic acids may be used either singly or in the form of a combination of two or more members. Among other monocarboxylic acids cited above, acrylic acid and methacrylic acid, particularly acrylic acid, prove to be particularly desirable from the viewpoint of the photocuring property.

Typical examples of the aforementioned acid anhydrides are dibasic acid anhydrides such as maleic anhydride, succinic anhydride, itaconic anhydride, phthalic anhydride, tetrahydrophtalic anhydride, hexahydrophthalic anhydride, methylhexahydrophthalic anhydride, endomethylene-tetrahydrophthalic anhydride, methylendomethylene-tetrahydrophthalic anhydride, chlorendic anhydride, and methyltetrahydrophthalic anhydride; aromatic polycarboxylic anhydrides such as trimellitic anhydride, pyromellitic anhydride, and benzophenone-tetracarboxylic dianhydride; and polycarboxylic anhydride derivatives such as 5-(2,5-dioxotetrahydrofuryl)-3-methyl-3-cyclohexene-1, 2-dicarboxylic anhydride.

The copolymers which are base polymers of the resins (2) and (3) mentioned above are obtained by using as monomers such alkyl (meth)acrylates and glycidyl (meth)acrylates or further hydroxyalkyl (meth)acrylates and copolymerizing these monomers by any of the well-known methods such as, for example, the method of solution polymerization.

The alkyl (meth)acrylates mentioned above are alkyl esters of acrylic acid or methacrylic acid. The alkyl group of the alkyl esters is an aliphatic hydrocarbon radical having from 1 to 6 carbon atoms. Examples of alkyl (meth)acrylates include, but are not limited to: esters of acrylic acid or methacrylic acid with methyl, ethyl, propyl, isopropyl, butyl, or hexyl.

The hydroxyalkyl (meth)acrylates mentioned above are hydroxyalkyl esters of acrylic acid or methacrylic acid. The hydroxyalkyl group of these hydroxyalkyl esters is desired to be an aliphatic hydrocarbon radical having from 1 to 6 carbon atoms and containing a primary hydroxyl group. The reason for this desirability is that it is desirable to select and use a hydroxyalkyl (meth)acrylate having a primary hydroxyl group as one of the component monomers of the aforementioned copolymer from the viewpoint of the ease with which the product of the reaction of the copolymer with (meth)acrylic acid is caused to react further with a polybasic acid anhydride. As typical examples of the hydroxyalkyl (meth)acrylates having a primary hydroxyl group, 2-hydoxyethyl acrylate, 2-hydroxyethyl methacrylate, etc. may be cited. It should be noted, however, that these are not exclusive examples.

In the copolymer as the basis of the resin (2) mentioned above, the molar ratio of an alkyl (meth)acrylate to glycidyl (meth)acrylate is desired to be in the range of from 40:60 to 80:20. In the copolymer as the basis of the resin (3) mentioned above, the molar ratio of hydroxyalkyl (meth)acrylate to an alkyl (meth)acrylate to glycidyl (meth)acrylate is desired to be in the range of 10–50:10–70:20–60, preferably in the range of 15–30:30–50:30–50. If the proportion of glycidyl (meth)acrylate to the copolymer is unduly low from the lower limits of the ranges mentioned above, the copolymer will be at a disadvantage in acquiring an unduly low photocuring property. Conversely, if this proportion exceeds the upper limits of the ranges mentioned above, the copolymer will be at a disadvantage in failing to allow the reaction of synthesis of a photosensitive resin to proceed smoothly.

The degree of polymerization of the copolymer obtained by copolymerizing the component monomers, as expressed by weight-average molecular weight, is desired to be in the range of from 10,000 to 70,000, preferably from 20,000 to 60,000. If the weight-average molecular weight is less than 10,000, the composition containing the resin will be at a disadvantage in acquiring unduly low dryness to the touch of finger. Conversely, if it exceeds 70,000, the composition will be at a disadvantage in acquiring an unduly low .developing property.

In the photocurable and thermosetting coating composition of the present invention, such vinyl compounds as styrene and methylstyrene may be used in a proportion not so large as to adversely affect the characteristic properties of the composition in addition to the component monomers mentioned above.

Typical examples of the photopolymerization initiators (B) mentioned above include benzoin and alkyl ethers thereof such as benzoin, benzoin methyl ether, benzoin ethyl ether, and benzoin isopropyl ether; acetophenones such as acetophenone, 2,2-dimethoxy-2-phenyl acetophenone, 2,2-diethoxy-2-phenyl acetophenone, 1,1-dichloroacetophenone, 1-hydroxycyclohexyl phenyl ketone, 2-methyl-1-[4-(methylthio)phenyl]-2-morpholinopropane- 1-on, 2-benzyl-2-dimethylamino-1-(4-morpholinophenyl)-1-butanone; anthraquinones such as 2-methylanthraquinone, 2-ethylanthraquinone, 2-t-butyl anthraquinone, 1-chloroanthraquinone, and 2-amylanthraquinone; thioxanthones such as 2,4-dimethylthioxanthone, 2,4-diethylthioxanthone, 2-chlorothioxanthone, and 2,4-diisopropylthioxanthone; ketals such as acetophenone dimethyl ketal and benzyl dimethyl ketal; benzophenones such as benzophenone; and xanthones. These photopolymerization initiators may be used either singly or in the form of a combination of two or more members. Optionally such a photopolymerization initiator (B) may be used in combination with one or more well-known conventional photopolymerization accelerators such as of the benzoic acid type and the tertiary amine type.

The amount of the photopolymerization initiator (B) to be used suitably falls in the range of from 0.2 to 30 parts by weight, preferably from 2 to 20 parts by weight, based on 100 parts by weight of the radiation-curable resin (A) mentioned above. If the amount of the photopolymerization initiator to be used is less than 0.2 part by weight, the composition will suffer from inferior photocuring property. Conversely, if the amount exceeds 30 parts by weight, the composition will entail the disadvantage of exhibiting inferior quality for cured film and poor stability during storage.

As the diluent (C) mentioned above, a photopolymerizable monomer and/or an organic solvent may be used.

Typical examples of photopolymerizable monomers include 2-hydroxypropyl acrylate, 2-hydroxyethyl acrylate, N-vinylpyrrolidone, acryloyl morpholine, methoxytetraethylene qlycol acrylate, methoxypolyethylene glycol acrylate, polyethylene glycol diacrylate, N,N-dimethyl acrylamide, N-methylol acrylamide, N,N-dimethylaminopropyl acrylamide, N,N-dimethylaminoethyl acrylate, N,N-dimethylaminopropyl acrylate, melamine acrylate, diethylene glycol diacrylate, triethylene glycol diacrylate, propylene glycol diacrylate, dipropylene glycol diacrylate, tripropylene glycol diacrylate, polypropylene glycol diacrylate, phenoxyethyl acrylate, tetrahydrofurfuryl acrylate, cyclohexyl acrylate, trimethylol propane diacrylate, trimethylol propane triacrylate, glycerin diglycidyl ether diacrylate, glycerin triglycidyl ether triacrylate, pentaerythritol triacrylate, pentaerythritol tetraacrylate, dipentaerythritol pentaacrylate, dipentaerythritol hexaacrylate, isobomeolyl acrylate, cyclopentadiene mono- or di-acrylate, methacrylates corresponding to the acrylates enumerated abvoe, and mono-, di-, tri-, and higher polyesters of polybasic acids with hydroxyalkyl (meth)acrylates.

As for the organic solvent, ketones, aromatic hydrocarbons, cellosolves, carbitols, glycol ethers, and acetates as mentioned above may be used.

The diluents (C) enumerated above can be used either singly or in the form of a mixture of two or more members. The amount of the diluent to be used is desired to fall in the range of 30 to 300 parts by weight, preferably 50 to 200 parts by weight, based on 100 parts by weight of the radiation-curable resin (A) mentioned above.

Here, the aforementioned photopolymerizable monomer is used for the purpose of diluting the aforementioned radiation-curable resin thereby rendering the produced composition easily applicable, and imparting photopolymerizability upon the comosition. The amount of the monomer to be used is desired to fall in the range of 3 to 50 parts by weight, based on 100 parts by weight of the radiation-curable resin (A) mentioned above. If the amount of the monomer is less than 3 parts by weight, the composition will be at a disadvantage in failing to enhance the photocuring property. Conversely, if the amount exceeds 50 parts by weight, the composition will be at a disadvantage in failing to heighten dryness to the tack-free touch of finger.

The organic solvent is used for the purpose of dissolving and diluting the radiation-curable resin (A) mentioned above, allowing the resin to be applied in the from of a liquid, enabling the applied layer of the liquid to form a film by the drying, and allowing the film to be exposed to light by the so-called "contact type exposure".

As concrete examples of the epoxy resin (D) to be used in the photocurable and thermosetting resin composition, the epoxy resins enumerated as concrete examples of the epoxy resin for use in the thermosetting resin composition may be cited. Among other epoxy resins enumerated above, it is desirable to use as a main component a finely powdered epoxy resin which exhibits sparing solubility in an organic solvent, such as bis-phenol S type epoxy resins represented by the product of Nippon Kayaku Co., Ltd. marketed under trademark designation of "EBPS"-200, that of Asahi Denka Kogyo K.K. under trademark designation of "EPX"-30, and that of Dai-Nippon Ink & Chemicals, Inc. under trademark designation of "EPICLON" EXA-1514; diglycidyl terephthalate resin represented by the product of Nippon Oil and Fats Co., Ltd. under trademark designation of "BLEMMER"-DGT; triglycidyl isocyanurate represented by the products of Nissan Chemical Industries, Ltd. under trademark designation of "TEPIC" and "TEPIC-H" and that of Ciba-Geigy Ltd. under trademark designation of "ARALDITE" PT810; and bixylenol type or biphenol type epoxy resins represented by the products of Yuka-Shell K.K. under trademark designation of "EPIKOTE" YX-4000 and YL-6121. The epoxy resins may be used either singly or in the form of a combination of two or more members.

The amount of the epoxy resins to be incorporated in the composition as a thermosetting component is desired to be in the range of 5 to 100 parts by weight, preferably 15 to 60 parts by weight, based on 100 parts by weight of the radiation-curable resin (A) mentioned above.

The amount of the cyanoguanidine derivative to be incorporated in the photocurable and thermosetting resin composition of the present invention is desired to be in the range of from 0.5 to 5 parts by weight, based on 100 parts by weight of the radiation-curable resin (A) mentioned above. If the amount is less than 0.5 part by weight, the incorporated cyanoguanidine derivative will fail to manifest the thermosetting property as expected. Conversely, if the amount exceeds 5.0 parts by weight, the excess will entrain the drawback that the photocurable and thermosetting resin composition prepared in a single liquid formulation suffers from a decrease of shelf life and the formed solder resist film incurs deterioration of electrical properties (insulation resistance).

The thermosetting resin composition and the photocurable and thermosetting resin composition of the present invention, when necessary, may incorporate therein any of well-known epoxy resin curing accelerators or promotors for the purpose of promoting the curing reaction of the epoxy resin with the cyanoguanidine derivative. Examples of the epoxy resin curing promotors include, but are not limited to: imidazole and imidazole derivatives such as 2-methylimidazole, 2-ethylimidazole, 2-ethyl-4-methylimidazole, 2-phenylimidazole, 4-phenylimidazole, 1-cyanoethyl-2-phenylimidazole, 1-(2-cyanoethyl)-2-ethyl-4-methylimidazole; guanamines such as acetoguanamine and benzoguanamine; and amines such as benzyldimethyl amine, 4-(dimethylamino)-N,N-dimethylbenzyl amine, 4-methoxy-N,N-dimethylbenzyl amine, and 4-methyl-N,N-dimethylbenzyl amine. The promotors which are commercially available include products of Shikoku Chemicals Co., Ltd. marketed under trademark designation of "CUREZOL" 2MZ-A, 2MZ-OK, 2PHZ, 2P4BHZ, and 2P4MHZ (invariably imidazole type compounds) and products of Sun-Apro K.K. marketed under product codes of U-CAT3503X, U-CAT3502X (invariably isocyanate compounds blocked with dimethyl amine), for example.

When only the cyanoguanidine derivative mentioned above is added to the composition as an epoxy resin curing agent, the reaction in the post-curing treatment begins at such a high temperature as about 200° C. It is, therefore, desired to lower the reaction starting temperature by having an epoxy resin curing accelerator incorporated in the composition. If this accelerator is incorporated in an unduly large amount, the excess of the accelerator will entrain the drawback of shortening the shelf life of the photocurable and thermosetting resin composition prepared in a single liquid formulation. The amount of the epoxy resin curing accelerator to be incorporated in the composition, therefore, is desired to be in the range of from 0.1 to 2.0 parts by weight, based on 100 parts by weight of the radiation-curable resin (A) mentioned above.

Further, the thermosetting or the photocurable and thermosetting coating composition of the present invention may incorporate therein, depending on the desired properties thereof, a well known and widely used filler such as barium sulfate, silicon oxide, talc, clay, calcium carbonate, silica, kaolin, glass fiber, carbon fiber, mica, asbestos, and metal powder; a color pigment such as phthalocyanine blue, phthalocyanine green, titanium oxide, and carbon black; a thickening agent such as bentonite, organo-bentonite and finely powdered silica; an anti-foaming agent; an adhesiveness-imparting agent; a leveling agent; and a well known and widely used thermal polymerization inhibitor such as hydroquinone, hydroquinone monomethyl ether, pyrogallol, t-butyl catechol, and phenothiazine.

The photocurable and thermosetting coating composition which is prepared in accordance with the present invention is adjusted, when necessary, to a level of viscosity suitable for the coating method, applied by the technique of screen printing, curtain coating, spray coating, roll coating, or the like to a printed circuit board having a circuit already formed thereon, for example, and then dried at a temperature in the range of from 60° to 100° C., for example, thereby to evaporate the organic solvent from the coated composition and give rise to a tack-free coating film. Then, the composition coated on the printed circuit board is selectively exposed to an actinic ray through a photomask having a prescribed pattern and the composition in the unexposed areas of the coating film is developed with a dilute aqueous alkali solution to obtain a resist pattern. Thereafter, the photocured coating film is further thermally cured by subjecting to the heat treatment at a temperature in the range of from 140° to 200° C., for example. By this thermal treatment, in addition to the curing reaction of the aforementiond thermosetting components, the polymerization of the photocurable resin components is promoted and the copolymerization of this component with the thermosetting component are also facilitated so that the consequently produced resist film acquires improvements in various properties such as resistance to heat, resistance to solvents, resistance to acids, adhesiveness, electrical properties, and hardness. The composition proves particularly useful for the formation of a solder resist.

As an aqueous alkali solution to be used in the process of development mentioned above, aqueous alkali solutions of potassium hydroxide, sodium hydroxide, sodium carbonate, potassium carbonate, sodium phosphate, sodium silicate, ammonia, amines, etc. can be used.

Examples of light sources which are advantageously used for the purpose of photocuring the composition include low-pressure mercury lamp, medium-pressure mercury lamp, high-pressure mercury lamp, ultra-high-pressure mercury lamp, xenon lamp, and metal halide lamp, for example. Also, a laser beam may be used as the actinic ray for exposure of the film.

Now, the present invention will be more specifically described below with reference to working examples. Wherever "parts" and "%" are mentioned hereinbelow, they invariably refer to those based on weight unless otherwise specified.

The abbreviations of cyanoguanidine derivatives used in the following working examples designate the following compounds.

ATU2CG: 3,9-bis(3-cyanoguanidinopropyl)-2,4,8,10-tetraoxaspiro[5.5]undecane having a substituent $R^2$ of (16) in the general formula (1a) mentioned hereinbefore.

2CG: 1,1-bis(3-cyanoguanidine) having a substituent $R^2$ of (2) in the general formula (1a).

Ph2CG: 1,4-bis(3-cyanoguanidino)benzene having a substituent $R^2$ of (6) in the general formula (1a).

DDM2CG: 4,4'-bis(3-cyanoguanidyl)diphenyl methane having a substituent $R^2$ of (7) in the general formula (1a).

HM2CG: 1,6-di($N^3$-cyano-$N^1$-guanidino)hexane having a substituent $R^2$ of (1) (n=6) in the general formula (1a).

MD: 2-cyanoguanidyl-4,6-diamino-S-triazine having a substituent $R^2$ of (35) in the general formula (1a).

EXAMPLE 1

The reactivity of a given cyanoguanidine derivative with in epoxy resin was determined by the use of a differential scanning calorimeter (DSC). As the epoxy resin, a product (epoxy equivalent weight 190) of Yuka-Shell K.K. marketed under trademark designation of Epikote 828 was used. The cyanoguanidine derivative as a curing catalyst and the epoxy resin were formulated in amounts such that the hydrogen atoms in the amino groups of the cyanoguanidine derivative accounted for 0.40 mol (1.0 mol in the case of MD) per mol of the epoxy group of the epoxy resin. They were mixed in a mortar. About 10 mg of the resultant mixture was charged in an aluminum container for the DSC, weighed accurately, and used as a sample of known weight. The analyzer was a differential scanning calorimetric analyzer produced by Seiko Denshi Kogyo K.K. and marketed under product code of "SSC5200". The analysis was carried out in the air atmosphere at a temperature increasing rate of 5° C./minute.

The results are shown in Table 1. In all the cyanoguanidine derivatives analyzed, the appearance of a conspicuous heat peak due to a curing reaction was recognized. From the cell after the heating, a brown cured mass was invariably obtained.

TABLE 1

| Compound | Reaction starting temperature (°C.) | Temperature of exothermic peak (°C.) | Exotherm (J/g) |
| --- | --- | --- | --- |
| ATU2CG | 138.4 | 184.8 | 371.7 |
| 2CG | 147.8 | 187.1 | 284.9 |
| Ph2CG | 208.2 | 249.3 | 251.8 |
| DDM2CG | 112.8 | 249.3 | 251.8 |
| HM2CG | 180.0 | 205.0 | 232.0 |
| MD | 155.9 | 216.1 | 469.1 |

EXAMPLE 2

The solubility of a given cyanoguanidine derivative in various organic solvents was determined. In an Erlenmeyer flask having an inner volume of 50 ml and fitted with a groundin stopper, 10 ml of a given organic solvent and a prescribed amount of the cyanoguanidine derivative were stirred at 25° C. for 30 minutes. The resultant mixture was filtered. The dissolved sample in the filtrate was isolated by vaporizing the solvent, dried and weighed. The solubility of the sample was calculated from the weight. The results are shown in Table 2.

TABLE 2

| Compound | Ethanol | MEK | Cyclohexane | Water |
| --- | --- | --- | --- | --- |
| ATU2CG | Trace | Trace | Trace | Trace |
| 2CG | Trace | Trace | Trace | Trace |
| Ph2CG | Trace | Trace | Trace | Trace |
| DDM2CG | Trace | Trace | Trace | Trace |
| MD | Trace | Trace | Trace | Trace |

It is clearly noted from Table 2 that the cyanoguanidine derivatives according to the present invention are sparingly soluble in the various organic solvents.

EXAMPLE 3

A sample was prepared by mixing 0.18 g of ATU2CG with 0.50 g of epoxy resin, Epikote 828 in a mortar and applying the resultant mixture in a thickness of 100 μm to a copper plate 8 mm in thickness (14×60 mm). The sample was heated in a furnace at 210° C. for 66 minutes to cure the applied coat. The cured coat in the sample thus obtained was tested for properties by the use of a knife edge type pendulum in a rigid-body pendulum type viscoelasticity tester (produced by Orientic Corp. and marketed under trademark designation of "Rheovibron DDV-OPA III"), with the temperature of the sample elevated from room temperature to 250° C. at a temperature increasing rate of 30° C./minute.

Samples of cured coats were obtained by following the procedure mentioned above while using 0.07 g of 2CG, 0.11 g of Ph2CG, 0.15 g of DDM2CG, and 0.07 g of MD respectively in place of 0.18 g of ATU2CG. They were tested for properties in the same manner as described above. The physical properties of the resultant cured coats are shown in Table 3.

TABLE 3

| | Physical properties of cured coat | |
| --- | --- | --- |
| Compound | Glass transition point (°C.) | Logarithmic damping factor (ln) |
| ATU2CG | 145 | 0.21 |
| 2CG | 175 | 0.08 |
| Ph2CG | 167 | 0.07 |
| DDM2CG | 171 | 0.08 |
| MD | 169 | 0.134 |

Figure 7:
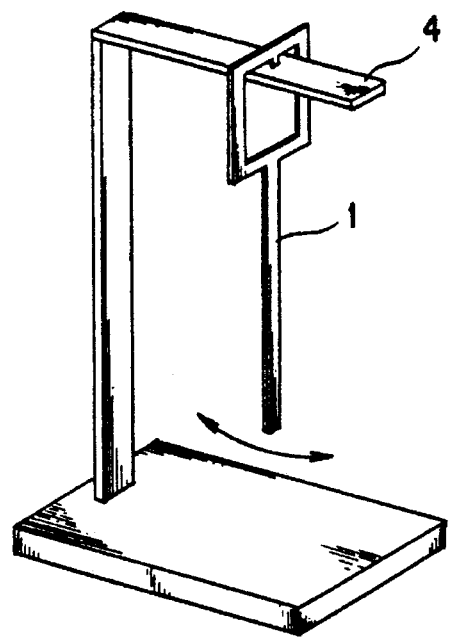
FIG. 7 is a schematic diagram showing the basic concept of the determination of logarithmic damping factor in Example 3.
Figure 8:
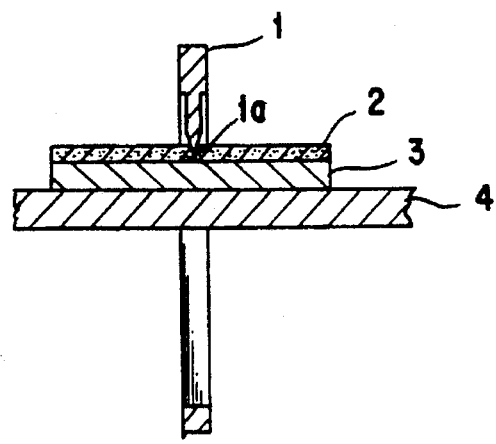
FIG. 8 is a fragmentary sectional view showing the state of determination of the logarithmic damping factor of a cured product by the use of an apparatus shown in FIG. 7.
Figure 9:
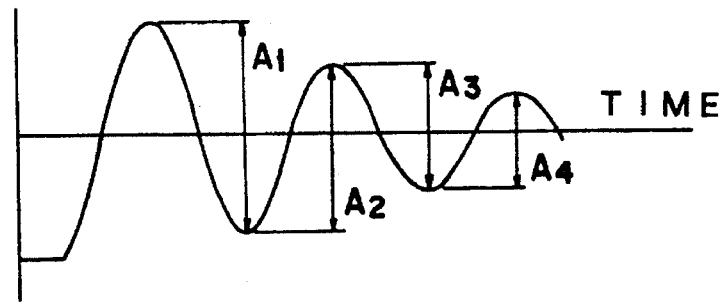
FIG. 9 is a schematic diagram showing the change in oscillation of a pendulum during the determination of the logarithmic damping factor in Example 3.

The logarithmic damping factor (Δ) indicated in Table 3 above denotes the magnitude which is obtained by mounting a rigid-body pendulum 1 on a substrate 3 covered with a coating 2 as shown in FIG. 7 and FIG. 8, heating a heat block 4 supporting the substrate 3 and meanwhile measuring the variation in the oscillation of the pendulum 1, and computing the following formula (9) using the data of variation of oscillation of the pendulum obtained as shown in FIG. 9. The pointed end 1a of the pendulum 1 penetrated the coating 2 and reached the surface of the substrate and functioned as a fulcrum of the oscillation.

$$\Delta = \frac{\ln\frac{A_1}{A_3} + \ln\frac{A_2}{A_4} + \ldots \ln\frac{A_n}{A_{n+2}}}{n} \quad (\ln) \quad (9)$$

The logarithmic damping factor is such that the softness of the cured coat increases in proportion as the magnitude of this factor increases. In all the samples used in the present example, that using ATU2CG produced the softest cured coat. This fact may be logically explained by a supposition that the effect of the flexibility of the substituent manifested itself in the cured coat. The samples using Ph2CG and DDM2CG clearly manifested the effects of their rigid aromatic rings. Incidentally, in the case of the cured coat using cyanoguanidine (abbreviation: CG), the glass transition point Tg is 166° C. and the logarithmic damping factor is 0.13. In the case of 2CG, the cured coat was fairly hard as compared with the cured coat using CG. This fact may be logically explained by a supposition that the number of cross-linking points increased.

EXAMPLE 4

Various cyanoguanidine derivatives were severally mixed with an epoxy resin (Epikote 828) so as to satisfy the ratio of 1 mol of active hydrogen equivalent weight per mol of the epoxy group of the epoxy resin. The compositions thus obtained were tested for variation of viscosity with time. The results are shown in Table 4 below.

TABLE 4

| | Variation of viscosity with time | |
| --- | --- | --- |
| Compound | Ratio of increase of viscosity by 7 days' standing at 50° C. (times) | Ratio of increase of viscosity by 1 month's standing at 25° C. (times) |
| CG (control) | 1.35 | 2.13 |
| HM2CG | 1.27 | 1.00 |
| 2CG | 4.90 | 3.27 |
| Ph2CG | 1.27 | 1.00 |

It is clearly noted from Table 4 that HM2CG and Ph2CG in particular were stable to resist the effect of aging.

EXAMPLE 5

The product of the reaction of (i) 1 equivalent weight of a cresol-novolak type epoxy resin having an epoxy equivalent weight of 220 and possessing an average of 7 phenol ring residues and epoxy groups per molecule thereof with (ii) 1.05 equivalent weight of acrylic acid, was caused to react with 0.67 equivalent weight of tetrahydrophthalic anhydride in carbitol acetate as a solvent under normal pressure. The product of this reaction was a viscous liquid containing 52 parts by weight of carbitol acetate, based on 100 parts by weight of solid resin. As a mixture, it showed an acid value of 63.4 mg KOH/g. Hereinafter, this product will be referred to for convenience as "resin A".

| Composition (a) | |
| --- | --- |
| Resin A | 152.0 parts |
| 2-Methyl-1-[4-(methylthio)phenyl]-2-morpholino-propane-1-on | 17.0 parts |
| Modaflow (trademark of Monsanto Co., U.S.A. for a leveling agent) | 3.0 parts |
| Silicone type anti-foaming agent (product of Shinetsu Chemical Industry Co., Ltd. | 4.0 parts |

27
-continued

| Composition (a) | |
|---|---|
| marketed under product code of KS-66) | |
| Fastogen Green S (trademark of Dainippon Ink and Chemicals Industries, Ltd. for a color pigment) | 1.5 parts |
| Aerosil #200 (trademark of Nippon Aerosil Co., Ltd for silica) | 2.0 parts |
| Barium sulfate | 65.0 parts |
| 2PHZ | 0.5 part |
| Product obtained in Synthesis Example 2 | 3.2 parts |
| Dipropylene glycol monomethyl ether | 2.0 parts |
| IPSOL #150 (trademark of Idemitsu Petrochemical Co., Ltd. for a solvent) | 2.0 parts |
| Total | 252.2 parts |

The above components were kneaded with a three-roll mill to prepare a main agent. As a cross-linking agent for this main agent, the following epoxy resin composition was similarly kneaded with a three-roll mill to prepare a hardener.

| Composition (b) | |
|---|---|
| N695 (product code of Dainippon Ink and Chemicals Industries, Ltd. for cresol novolak type epoxy resin) | 32.0 parts |
| Triglycidyl isocyanurate | 10.0 parts |
| DPHA (product code of Nippon Kayaku K.K. for a photopolymerizable monomer) | 20.0 parts |
| Dipropylene glycol monomethyl ether | 5.0 parts |
| IPSOL #150 | 5.0 parts |
| Barium sulfate | 35.0 parts |
| Total | 107.0 parts |

The main agent and the hardener prepared as described above were mixed in the following ratio to obtain a solder resist ink. The same mixing ratio of the hardener to the main agent was employed in the following Examples 6 to 8 and Comparative Example 1:

Main agent: hardener=70:30

EXAMPLE 6

A main agent was prepared by following the procedure of Example 5, except that 1.9 parts of the product obtained in Synthesis Example 4 was used in place of 3.2 parts of the product obtained in Synthesis Example 2. The hardener was same as that used in Example 5.

EXAMPLE 7

A main agent was prepared by following the procedure of Example 5, except that 2.6 parts of the product obtained in Synthesis Example 5 was used in place of 3.2 parts of the product obtained in Synthesis Example 2. The hardener was same as that used in Example 5.

EXAMPLE 8

A main agent was prepared by following the procedure of Example 5, except that 2.0 parts of hexamethylene-bis-cyanoguanidine was used in place of 3.2 parts of the product obtained in Synthesis Example 2. The hardener was same as that used in Example 5.

COMPARATIVE EXAMPLE 1

A main agent was prepared by following the procedure of Example 5, except that 1.0 part of cyanoguanidine was used in place of 3.2 parts of the product obtained in Synthesis Example 2. The hardener was same as that used in Example 5.

Evaluation of quality:

Each of the ink compositions obtained in Examples 5 to 8 and Comparative Example 1 was applied by the screen printing method onto the entire surface of a copper-clad substrate having a prescribed pattern formed in advance thereon and then dried at 80° C. for 20 minutes to give a tack-free coating film. Each coating film on the substrate was exposed to an actinic radiation according to a solder resist pattern through a negative film tightly superposed thereon to a dose of 800 mJ/cm$^2$ and then developed with an aqueous 1 wt % sodium carbonate solution for one minute to form a resist pattern thereon. The coating film on the substrate was thermally cured at 150° C. for 50 minutes to prepare a test substrate, which was tested for resistance to soldering temperature, acid resistance, alkali resistance, pencil hardness, and electrical property. The developing property and the storage stability of each ink composition mentioned above were determined by the methods to be described hereinafter.

(1) Test for drying time (developing property)

Each of the compositions obtained in the examples and the comparative example cited above was applied by the screen printing method onto the entire surface of a copper-clad substrate having a prescribed pattern formed in advance thereon and then predried at 80° C. for periods graduated at an interval of 10 minutes. The coating films consequently formed on the substrates were exposed to an actinic radiation according to a solder resist pattern through a negative film tightly superposed thereon. They were then developed with an aqueous 1 wt % sodium carbonate solution for one minute to test for life (the longest drying period allowing effective development).

(2) Resistance to soldering temperature

A given test substrate was coated with a rosin type flux, immersed for 30 seconds in a soldering bath set in advance at 260° C., washed with propylene glycol monomethylether acetate and ethanol for removal of the flux, and visually examined as to swelling and discoloration of the resist layer. The test substrates was further subjected to a peel test using a cellophane adhesive tape as to the peeling of the resist layer. The rating was made on the following three-point scale.

○: Perfect absence of any discernible change

Δ: Only slight change of the resist layer x: Presence of discernible swelling, peeling or discoloration of the resist layer (3) Acid resistance A given test substrate was immersed for 30 minutes in an aqueous 10 wt % sulfuric acid solution at normal room temperature, washed with water, and then subjected to a peel test using a cellophane adhesive tape to find the extents of peeling and discoloration consequently produced in the resist layer. They were rated on the following three-point scale.

○: Perfect absence of any discernible change

Δ: Slight change of the resist layer x: Presence of discernible swelling, peeling or discoloration of the resist layer

(4) Alkali resistance

A given test substrate was immersed for 30 minutes in an aqueous 10 wt % sodium hydroxide solution at normal room temperature, washed with water, and then subjected to a peel test using a cellophane adhesive tape to find the extents of peeling and discoloration consequently produced in the resist layer. They were rated on the following three-point scale.

○: Perfect absence of any discernible change

Δ: Slight change of the resist layer x: Presence of discernible swelling, peeling or discoloration of the resist layer

(5) Pencil hardness

In accordance with the testing method of JIS K-5400 6.14 using a pencil hardness tester, a given test substrate was placed under a load of 1 kg. This property was reported by the highest hardness which inflicted no dent on the coating. The pencils used for this test were "Mitsubishi® Hi-Uni" made by Mitsubishi Pencil Co., Ltd. (registered trademark).

(6) Electrical property

This property was determined by preparing a test substrate under the conditions mentioned above using a comb type electrode B coupon of IPC SM-840B B-25, applying a bias voltage of DC 500 V to the comb type electrode, and measuring the initial insulation resistance. This test substrate was left standing for 12 hours under the conditions of 121° C., 100% R.H., and two atmospheric pressure so as to be humidified. After humidification, the insulation resistance of the test substrate was determined in the same manner as described above. This insulation resistance is denoted in Table 5 as "after PCT". Another test substrate prepared in the same manner as described above was also subjected to humidification and measurement of the insulation resistance in the same manner as described above, except that a bias voltage of DC 100 V was applied thereto. This insulation resistance is denoted in Table 5 as "after PCBT".

(7) Storage stability

After the main agent was mixed with the hardener, the resultant ink composition was left standing in a thermostatic chamber kept at 40° C. for one week and then examined to find the extents of change in viscosity and evaluate stability during storage. The storage stability was rated on the following three-point scale.

○: Change of viscosity less than 1.5 times the initial value

Δ: Change of viscosity not less than 1.5 times and less than 3 times the initial value x: Change of viscosity not less than 3 times the initial value The results of these evaluations are shown in Table 5.

TABLE 5

| Characteristic properties | Example 5 | Example 6 | Example 7 | Example 8 | Comparative Example 1 |
|---|---|---|---|---|---|
| (1) Drying time (min.) (Developing property) | 120 | 120 | 120 | 120 | 100 |
| (2) Resisrance to soldering temp. | ○ | ○ | ○ | ○ | ○ |
| (3) Acid resistance | ○ | ○ | ○ | ○ | ○ |
| (4) Alkali resistance | ○ | ○ | ○ | ○ | ○ |
| (5) Pencil hardness | 6H | 6H | 6H | 6H | 6H |
| (6) Electrical property, insulation resistance (Ω) | | | | | |
| Initial value | $10^{12}$ | $10^{12}$ | $10^{12}$ | $10^{12}$ | |
| After PCT | $10^{12}$ | $10^{12}$ | $10^{12}$ | $10^{12}$ | |
| After PCBT | $10^{12}$ | $10^{12}$ | $10^{12}$ | $10^{12}$ | |
| (7) Storage stability | ○ | ○ | ○ | ○ | x |

EXAMPLE 9

| Composition (a) | |
|---|---|
| Resin A | 150.0 parts |
| Silicone type anti-foaming agent (KS-66) | 2.0 parts |
| 2-Methyl-1-[4-(methylthio)phenyl]-2-morpholino-propane-1-on | 16.0 parts |
| Fastogen Green S | 5.0 parts |
| Dipropylene glycol monomethyl ether | 4.0 parts |
| IPSOL #150 | 3.0 parts |
| Barium sulfate | 30.0 parts |
| Finely powdered silica | 30.0 parts |
| Product obtained in Synthesis Example 3 | 8.0 parts |
| Total | 248.0 parts |

The above components were kneaded with a three-roll mill to prepare a main agent. As a cross-linking agent for this main agent, the following epoxy resin composition was similarly kneaded with a three-roll mill to prepare a hardener.

| Composition (b) | |
|---|---|
| Dipropylene glycol monomethyl ether | 12.0 parts |
| IPSOL #150 | 12.0 parts |
| DPHA | 24.0 parts |
| Triglycidyl isocyanurate | 26.0 parts |
| YX-4000 | 26.0 parts |
| Barium sulfate | 50.0 parts |
| Total | 150.0 parts |

The main agent and the hardener prepared as described above were mixed in the ratio of 70:30 to obtain a solder resist ink.

COMPARATIVE EXAMPLE 2

A main agent was prepared by following the procedure of Example 9, except that 6.0 parts of melamine was used in place of 8.0 parts of the product obtained in Synthesis Example 3. The hardener was same as that used in Example 9.

Each of the ink compositions obtained in Example 9 and Comparative Example 2 was tested for electroless gold plating resistance as described below.
Electroless gold plating resistance:

The copper plane of a copper plated-throughhole printed circuit board having a prescribed pattern formed in advance thereon was surface-treated by (a) jet-scrub polishing with the use of an abrasive No. 270 (manufactured by Ishii Hyoki K.K.), washing with water and drying or (b) polishing with the use of a roll buff No. 1200 (manufactured by Ishii Hyoki K.K.), washing with water and drying. The resultant board was subjected to coating, drying, exposure, development and heating in the same manner as described above to thereby give a test piece. By using this test piece, electroless gold plating was effected by the method as specified below. Then the test piece was subjected to a peel test with the use of an adhesive cellophane tape and peeling conditions of the resist layer were evaluated on the following three-point scale.

○: Neither any change in appearance nor peeling of the resist layer was observed.

Δ: No change in appearance was observed, though slight peeling of the resist layer was observed.

x: The resist layer suffered from lifting and plating penetration, and significant peeling of the resist layer was observed in the peeling test.

Method for electroless gold plating:

The test piece was degreased by dipping in an acidic degreasing solution (a 20% by vol. solution of Metex L-5B manufactured by Fuji Chemical Industries Co., Ltd.) at 30° C. for 3 minutes and then washed with water by dipping in running water for 3 minutes. Next, the test piece was subjected to soft etching by dipping in an aqueous 14.3 wt % ammonium persulfate solution at room temperature for 3 minutes and then washed with water by dipping in running water for 3 minutes. After dipping in an aqueous 10% by vol. sulfuric acid solution for one minute at room temperature, the test piece was washed with water by dipping in running water for 30 seconds to one minute. Then it was dipped in a catalyst solution (a 10% by vol. aqueous solution of Metal plate Activator 350 manufactured by Meltex Inc.) at 30° C. for 7 minutes to thereby add the catalyst thereto and then washed with water by dipping in running water for 3 minutes. This test piece having the catalyst added thereto was subjected to electroless nickel plating by dipping in a nickel plating solution (a 20% by vol. aqueous solution of Melplate Ni-865M, manufactured by Meltex Inc., pH 4.6) at 85° C. for 20 minutes. After dipping in an aqueous 10% by vol. sulfuric acid solution at room temperature for one minute, the test piece was washed with water by dipping in running water for 30 seconds to one minute. Next, the test piece was subjected to electroless gold plating by dipping in a gold plating solution (an aqueous solution of 15% by vol. of Aurolectroless UP manufactured by Meltex Inc. and 3% by vol. of gold potassium cyanide, pH 6) at 95° C. for 10 minutes. Then it was washed with water by dipping in running water for 3 minutes and with hot water by dipping in hot water at 60° C. for 3 minutes. After sufficient washing with water, thorough draining, and drying, an electroless gold plated test piece was obtained. The results are shown in Table 6.

TABLE 6

| Characteristic | Example 9 | Comparative Example 2 |
|---|---|---|
| Electroless gold plating resistance | ○ | Δ |

While certain specific working examples have been disclosed herein, the invention may be embodied in other specific forms without departing from the spirit or essential characteristics thereof. The described examples are therefore to be considered in all respects as illustrative and not restrictive, the scope of the invention being indicated by the appended claims rather than by foregoing description and all changes which come within the meaning and range of equivalency of the claims are, therefore, intended to be embraced therein.

What is claimed is:

1. A cyanoguanidine derivative represented by the following general formula (1):

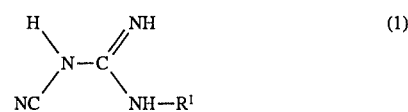

(1)

wherein $R^1$ represents a substituent selected from the group consisting of the following substituents: (a) through (i)

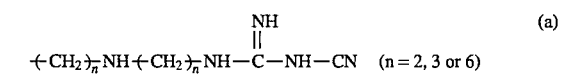

(a)

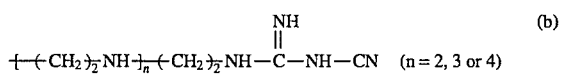

(b)

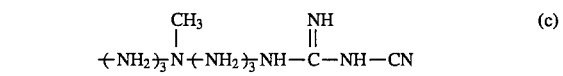

(c)

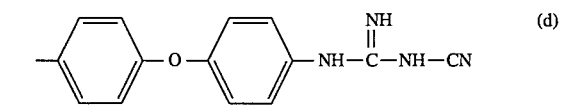

(d)

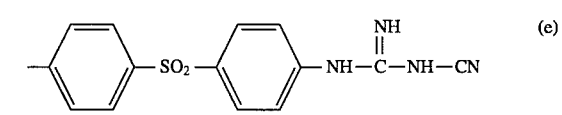

(e)

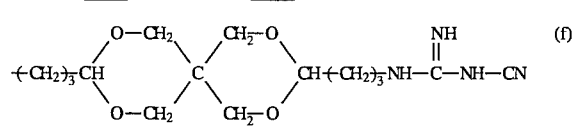

(f)

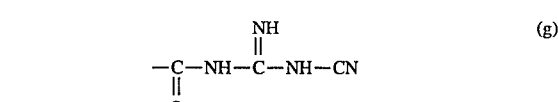

(g)

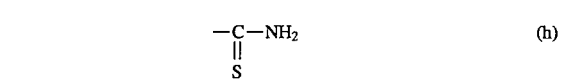

(h)

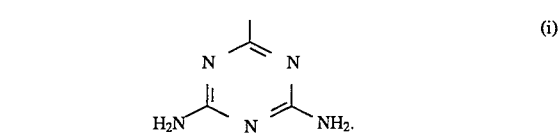

(i)

2. The cyanoguanidine derivative according to claim 1, which is represented by the following formula:

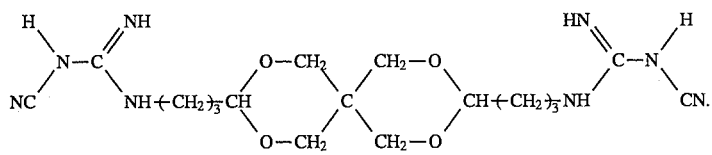
3. The cyanoguanidine derivative according to claim 1, which is represented by the following formula:
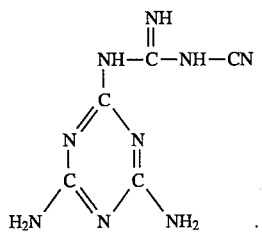
4. An epoxy resin curing agent represented by the following formula (1a):
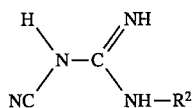
wherein R² represents a substituent selected from the group consisting of the following substituents:
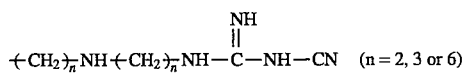 (1)
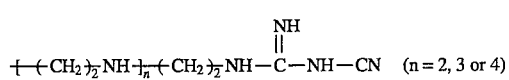 (2)
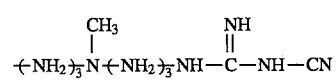 (3)
 (4)
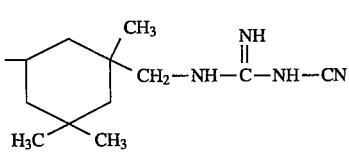 (5)
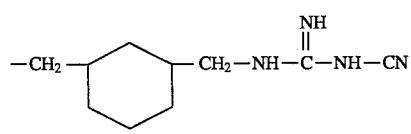 (6)
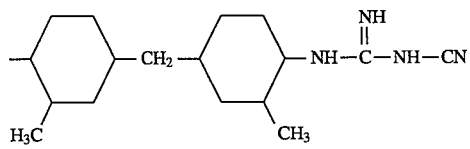 (7)
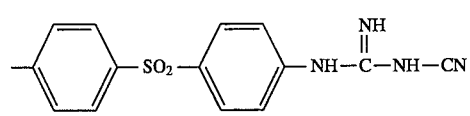 (8)
-continued
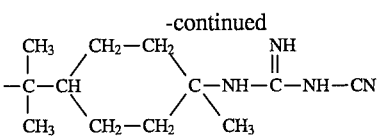 (9)
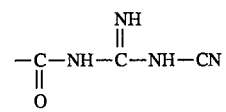 (10)
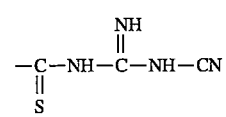 (11)
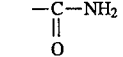 (12)
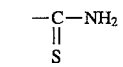 (13)
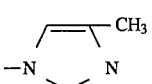 (14)
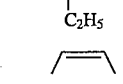 (15)
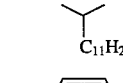 (16)
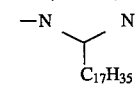 (17)
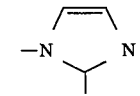 (18)
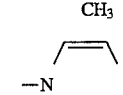 (19)
 (20)

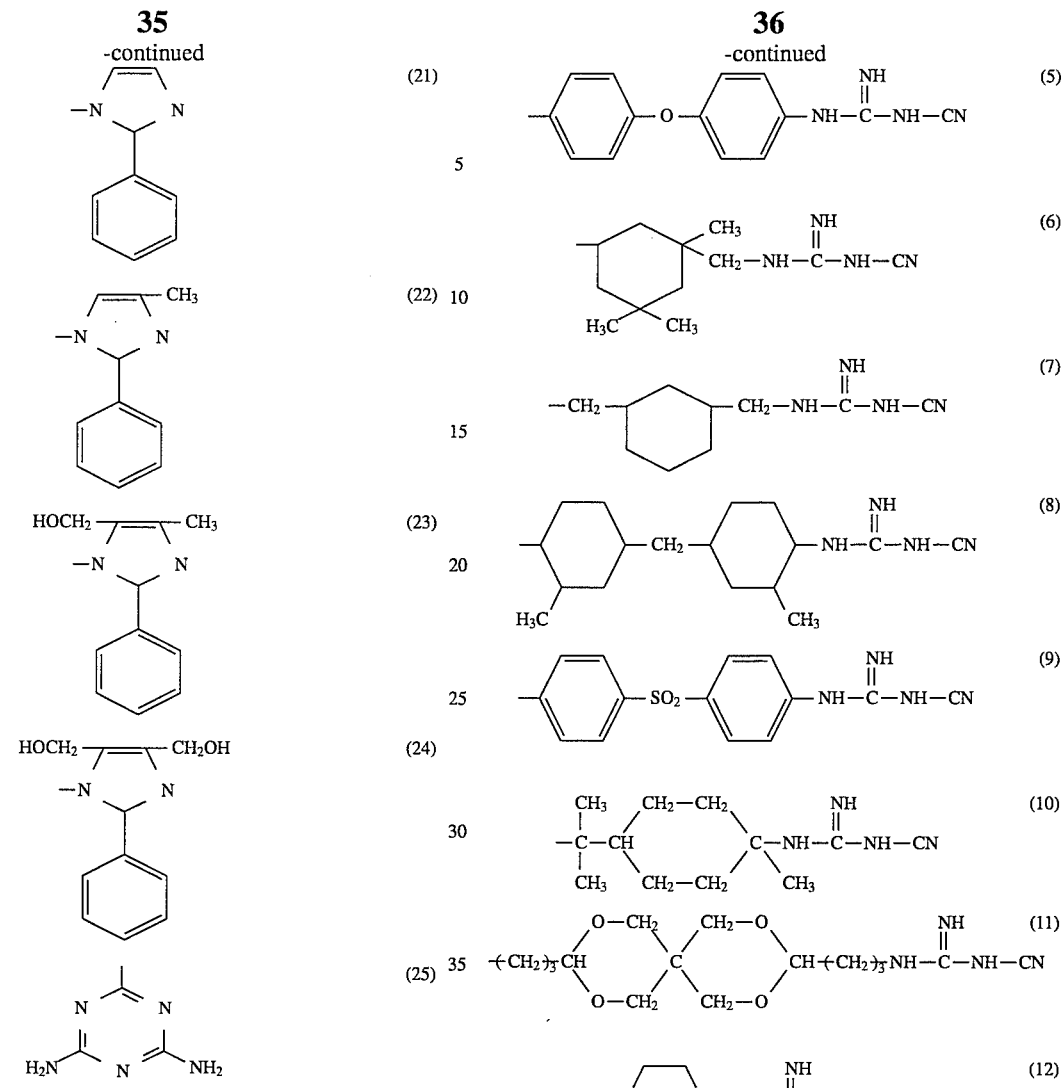
5. A thermosetting resin composition, comprising (a) an epoxy resin and (b) an epoxy resin curing agent represented by the following formula (1a):
$$\begin{array}{c} H \\ | \\ NC \end{array} N - C \begin{array}{c} NH \\ \| \\ NH - R^2 \end{array} \quad (1a)$$
wherein $R^2$ represents a substituent selected from the group consisting of the following substituents:

37
-continued

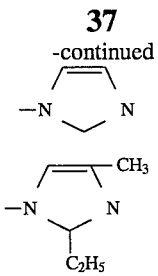

(19)

(20) 5

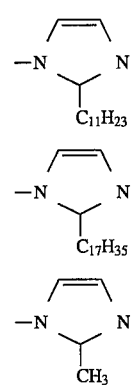

10
(21)

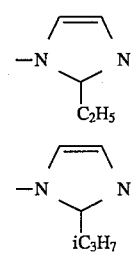

(22)

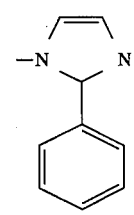

(23)

20

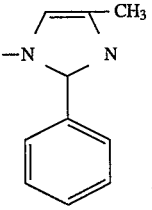

(24)

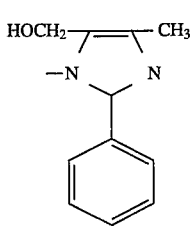

25

(25) 30

(26)

(27) 45

(28) 55

60

65

38
-continued

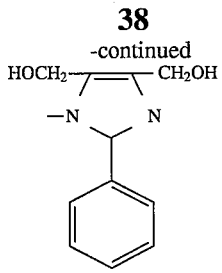 (29)

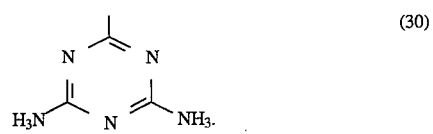 (30)

6. The composition according to claim 5, wherein said epoxy resin is at least one member selected from the group consisting of glycidyl ethers of bis-phenol A or brominated bis-phenol A, glycidyl ethers of novolak resins, glycidyl ethers of bis-phenol F, glycidyl ethers of bis-phenol S, alicyclic epoxy resins, glycidyl ester resins, amine compounds having glycidyl groups, epoxy resins having glycidyl groups linked to a hydantoin ring, triglycidyl isocyanurate, glycidyl ethers of bixylenols, and glycidyl ethers of biphenols.

7. The composition according to claim 5, which further comprises an organic solvent.

8. The composition according to claim 5, which further comprises an epoxy resin curing promotor.

9. The composition according to claim 5, which further comprises an inorganic filler.

10. The composition according to claim 5, which further comprises a color pigment.

11. The composition according to claim 5, which further comprises a thermopolymerization inhibitor.

12. The composition according to claim 5, which further comprises a thickening agent.

13. The composition according to claim 5, which further comprises an anti-foaming agent.

14. The composition according to claim 5, which further comprises a leveling agent.

15. A photocurable and thermosetting resin composition, comprising:

(A) a resin curable by active energy radiation, which has at least two ethylenically unsaturated bonds in combination with a carboxyl group in the molecular unit thereof, (B) a photopolymerization initiator, (C) a diluent, (D) an epoxy resin, and (E) an epoxy resin curing agent, the epoxy resin curing agent (E) being a cyanoguanidine derivative represented by the following formula (1b):

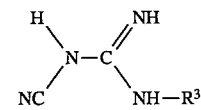 (1b)

wherein $R^3$ represents a substituent selected from the group consisting of the following substituents:

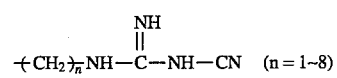 (1)

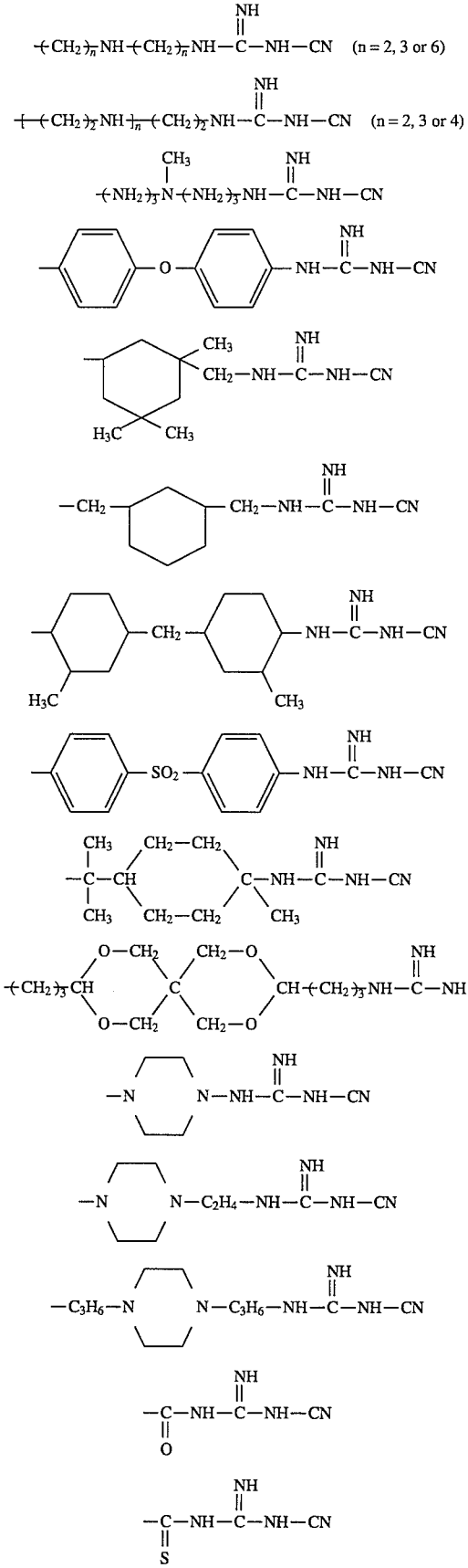
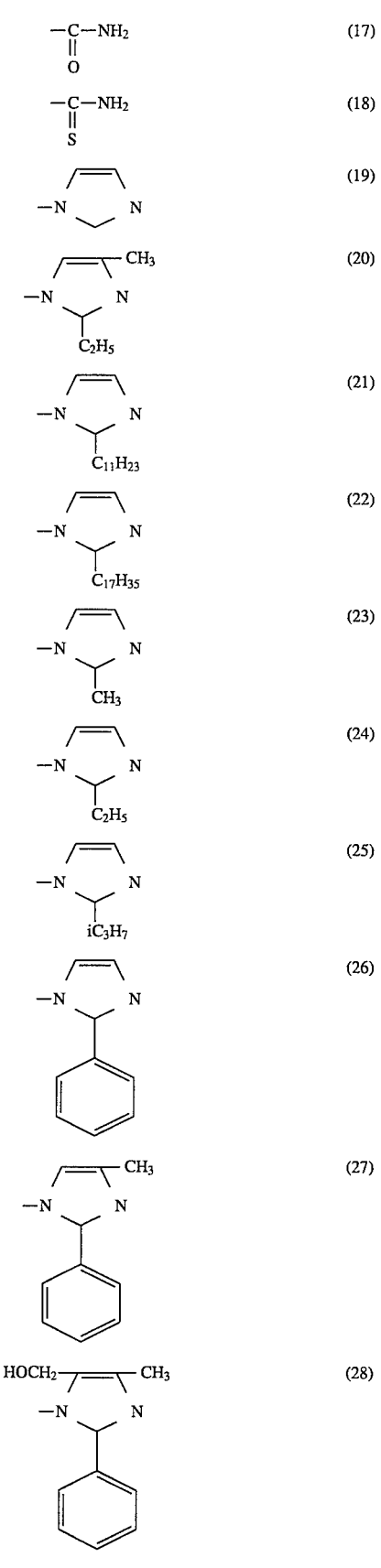

-continued

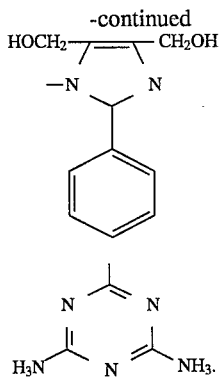

16. The composition according to claim 15, wherein said resin curable by the active energy radiation is a resin selected from the group consisting of (1) a reaction product obtained by reacting a polyfunctional glycidyl ether of novolak resin with an unsaturated monocarboxylic acid to form an esterified product and subsequently reacting the esterified product with a saturated or unsaturated polybasic acid anhydride, (2) a reaction product obtained by reacting (meth)acrylic acid with a copolymer composed of an alkyl (meth)acrylate and a glycidyl (meth)acrylate and subsequently reacting the resultant reaction product with a saturated or unsaturated polybasic acid anhydride, (3) a reaction product obtained by reacting (meth)acrylic acid with a copolymer composed of a hydroxyalkyl (meth)acrylate, an alkyl (meth) acrylate, and a glycidyl (meth)acrylate and subsequently reacting the resultant product with a saturated or unsaturated polybasic acid anhydride, and (4) a reaction product obtained by partially reacting a glycidyl (meth)acrylate with a copolymer composed of an alkyl (meth)acrylate and (meth)acrylic acid.

17. The composition according to claim 15, wherein said resin curable by the active energy radiation is a resin obtained by reacting at least 0.15 mol of a saturated or unsaturated polybasic acid anhydride with each hydroxyl group possessed by a reaction product of a polyfunctional glycidyl ether of novolak resin with an unsaturated monocarboxylic acid.

18. The composition according to claim 15, wherein said resin curable by the active energy radiation has an acid value falling in the range of from 40 to 160 mg KOH/g.

19. The composition according to claim 15, wherein said photopolymerization initiator is at least one compound selected from the group consisting of benzoin, alkyl ethers of benzoin, acetophenones, anthraquinones, ketals, benzophenones, thioxanthones, and xanthones and is used in a proportion in a range from 0.2 to 30 parts by weight, based on 100 parts by weight of said resin curable by the active energy radiation.

20. The composition according to claim 15, wherein said diluent is selected from organic solvents and photopolymerizable monomers and is used in a proportion in the range of from 30 to 300 parts by weight, based on 100 parts by weight of said resin curable by the active energy radiation.

21. The composition according to claim 15, wherein said epoxy resin is at least one member selected from the group consisting of glycidyl ethers of bis-phenol A or brominated bis-phenol A, glycidyl ethers of novolak resins, glycidyl ethers of bis-phenol S, alicyclic epoxy resins, glycidyl ester resins, amine compounds having glycidyl groups, epoxy resins having glycidyl groups linked to a hydantoin ring, triglycidyl isocyanurate, glycidyl ethers of bixylenols, and glycidyl ethers of biphenols.

22. The composition according to claim 15, wherein the amount of said epoxy resin to be incorporated in the composition is in the range of from 5 to 100 parts by weight, based on 100 parts by weight of said resin curable by the active energy radiation.

23. The composition according to claim 15, wherein the amount of said epoxy resin curing agent to be incorporated in the composition is in the range of from 0.5 to 5.0 parts by weight, based on 100 parts by weight of said resin curable by the active energy radiation.

24. The composition according to claim 15, which further comprises an epoxy resin curing promotor.

25. The composition according to claim 15, which further comprises an inorganic filler.

26. The composition according to claim 15, which further comprises a color pigment.

27. The composition according to claim 15, which further comprises a thermopolymerization inhibitor.

28. The composition according to claim 15, which further comprises a thickening agent.

29. The composition according to claim 15, which further comprises an anti-foaming agent.

30. The composition according to claim 15, which further comprises a leveling agent.

* * * * *